US012797141B2

(12) United States Patent
Simaan et al.

(10) Patent No.: US 12,797,141 B2
(45) Date of Patent: Nov. 17, 2026

(54) PERCEPTION FOR EFFECTIVE THROMBUS RETRIEVAL AND ANEURYSM EMBOLIZATION

(71) Applicant: Vanderbilt University, Nashville, TN (US)

(72) Inventors: Nabil Simaan, Nashville, TN (US); Colette P. Abah, Nashville, TN (US); Rohan V. Chitale, Nashville, TN (US); Haoxiang Luo, Nashville, TN (US)

(73) Assignee: VANDERBILT UNIVERSITY, Nashville, TN (US)

(*) Notice: Subject to any disclaimer, the term of this patent is extended or adjusted under 35 U.S.C. 154(b) by 146 days.

(21) Appl. No.: 18/570,025

(22) PCT Filed: Jun. 14, 2022

(86) PCT No.: PCT/US2022/033502
§ 371 (c)(1),
(2) Date: Dec. 13, 2023

(87) PCT Pub. No.: WO2022/266152
PCT Pub. Date: Dec. 22, 2022

(65) Prior Publication Data

US 2024/0277423 A1 Aug. 22, 2024

Related U.S. Application Data

(60) Provisional application No. 63/210,295, filed on Jun. 14, 2021.

(51) Int. Cl.
*A61B 34/00* (2016.01)
*A61B 17/00* (2006.01)
(Continued)

(52) U.S. Cl.
CPC .............. *A61B 34/25* (2016.02); *A61B 17/22* (2013.01); *A61B 2017/00115* (2013.01);
(Continued)

(58) Field of Classification Search
CPC . A61B 34/25; A61B 17/22; A61B 2034/2065; A61B 2090/064;
(Continued)

(56) References Cited

U.S. PATENT DOCUMENTS 11,045,271 B1 * 6/2021 Tran .......................... G16H 20/40
2012/0232020 A1 9/2012 Seelen
(Continued)

FOREIGN PATENT DOCUMENTS

WO 2014151209 A1 9/2014
WO WO-2019181632 A1 * 9/2019 ......... A61B 1/00048
WO 2021062527 A1 4/2021

OTHER PUBLICATIONS

Jankowitz B. et al., "Manual Aspiration Thrombectomy," Stroke, vol. 43, No. 5, pp. 1408-1411, 2012.
(Continued)

*Primary Examiner* — Kathleen S Holwerda
*Assistant Examiner* — Cherie M Poland
(74) *Attorney, Agent, or Firm* — MICHAEL BEST & FRIEDRICH LLP

(57) ABSTRACT

A novel approach for indirect endovascular sensing that equips surgeons with two capabilities: estimating the distance between the catheter tip and a target and evaluating the quality of the engagement of the catheter tip with the target, wherein applying flow and pressure excitation to a proximal end of the catheter; measuring a pressure change, with a pressure sensor in fluid communication with the catheter, at the proximal end of the catheter, the pressure change based on a cycle of applied proximal pressure excitation and
(Continued)

advancement of the catheter toward the target; applying a machine learning model to the measured pressure change to determine the distance between the tip of the catheter and the target; and providing the distance between the tip of the catheter and the target to a user.

19 Claims, 11 Drawing Sheets

(51) Int. Cl.
*A61B 17/22* (2006.01)
*A61B 34/20* (2016.01)
*A61B 90/00* (2016.01)

(52) U.S. Cl.
CPC ............... *A61B 2017/00292* (2013.01); *A61B 2034/2065* (2016.02); *A61B 2090/064* (2016.02)

(58) Field of Classification Search
CPC ........... A61B 2017/00115; A61B 2017/00292; A61B 90/061; A61B 5/6852; A61B 5/6886; A61B 5/7264; A61M 2025/0001
See application file for complete search history.

(56) References Cited

U.S. PATENT DOCUMENTS

| | | | | |
|---|---|---|---|---|
| 2014/0180135 | A1* | 6/2014 | Hoseit | A61B 5/0084 600/478 |
| 2014/0180239 | A1 | 6/2014 | Mittermeyer et al. | |
| 2018/0078195 | A1 | 3/2018 | Sutaria et al. | |
| 2019/0239910 | A1 | 8/2019 | Brady et al. | |
| 2019/0254564 | A1* | 8/2019 | Schwartz | A61B 5/066 |
| 2020/0138518 | A1* | 5/2020 | Lang | A61B 17/1703 |
| 2020/0281503 | A1* | 9/2020 | Salamini | A61B 5/068 |
| 2021/0128182 | A1 | 5/2021 | Teigen et al. | |
| 2021/0137634 | A1* | 5/2021 | Lang | A61B 90/00 |

OTHER PUBLICATIONS

Jovin, T. G., et al. "Thrombectomy within 8 hours after symptom onset in ischemic stroke." New England Journal of Medicine 372.24 (2015): 2296-2306.
Kadirvel R. et al., "Endovascular treatment of aneurysms: healing mechanisms in a Swine model are associated with increased expression of matrix metalloproteinases, vascular cell adhesion molecule-1, and vascular endothelial growth factor, and decreased expression of tissue i," AJNR. Am. J. Neuroradiol., vol. 28, No. 5, pp. 849-856, May 2007, [Online]. Available: http://www.ncbi.nlm.nih.gov/pubmed/17494655.
Kaiser, E. et al. "Sparse identification of nonlinear dynamics for model predictive control in the low-data limit," Proc. R. Soc. A Math. Phys. Eng. Sci., vol. 474, No. 2219, p. 20180335, Nov. 2018.
Kesner, S. B., et al. (May 2010). Design and control of motion compensation cardiac catheters. In 2010 IEEE international conference on robotics and automation (pp. 1059-1065). IEEE.
Khoshnam, M. et al. "Estimating contact force for steerable ablation catheters based on shape analysis." 2014 IEEE/RSJ International Conference on Intelligent Robots and Systems. IEEE, 2014.
Khoshnam, M., et al. (2015). Modeling and estimation of tip contact force for steerable ablation catheters. IEEE Transactions on Biomedical Engineering, 62(5), 1404-1415.
Kizilova, N.N. "Pressure wave propagation in liquid-filled tubes of viscoelastic material," Fluid Dyn., vol. 41, No. 3, pp. 434-446, 2006.
Krejza J. et al. "Carotid artery diameter in men and women and the relation to body and neck size," Stroke, vol. 37, No. 4, pp. 1103-1105, 2006.
Krueger, P. S. et al. "Vortex rings in bio-inspired and biological jet propulsion," CIMTEC 2008—Proc. 3rd Int. Conf. Smart Mater. Struct. Syst.—Min. Smartness from Nat., vol. 58, pp. 237-246, 2008.
Kuck, K.-H., et al. "A novel radiofrequency ablation catheter using contact force sensing: Toccata study." Heart rhythm 9.1 (2012): 18-23.
Kugelstadt T. et al. "Position and Orientation Based Cosserat Rods," Symp. Comput. Animat., vol. Jul. 11, pp. 169-178, 2016.
Kunz, W., et al. "O-001 Lifetime quality of life and cost consequences of treatment delays in endovascular thrombectomy for stroke based on hermes data." (2018): A1-A2.
Lampe, R. et al. "Mathematical Modelling of Cerebral Blood Circulation and Cerebral Autoregulation: Towards Preventing Intracranial Hemorrhages in Preterm Newborns," Comput. Math. Methods Med., vol. 2014, pp. 1-9, 2014.
Li, Z. et al., "A one-dimensional flow model enhanced by machine learning for simulation of vocal fold vibration," JASA, p. In press, 2021.
Liberson, A. S. et al. "A physics based approach to the pulse wave velocity prediction in compliant arterial segments," J. Biomech., vol. 49, No. 14, pp. 3460-3466, 2016.
Lima, F. O., et al. (2014). Prognosis of untreated strokes due to anterior circulation proximal intracranial arterial occlusions detected by use of computed tomography angiography. JAMA neurology, 71(2), 151-157.
Long T.D. et al., "Novel aspiration catheter design for acute stroke thrombectomy," J. Neurointerv. Surg., vol. 11, No. 2, pp. 179-183, 2019.
Luraghi G. et al., "Applicability assessment of a stent-retriever thrombectomy finite-element model," Interface Focus, vol. 11, No. 1, p. 20190123, 2021.
Marks M.P. et al., "Endovascular Treatment in the DEFUSE 3 Study," Stroke, vol. 49, No. 8, pp. 2000-2003, Aug. 2018.
Merritt W. et al., "Quantifying the mechanical and histological properties of thrombus analog made from human blood for the creation of synthetic thrombus for thrombectomy device testing," J. Neurointerv. Surg., vol. 10, No. 12, pp. 1168-1173, 2018.
Mikhal J. et al. "Pulsatile flow in model cerebral aneurysms," Procedia Comput. Sci., vol. 4, pp. 811-820, 2011.
Minimally Invasive Neurosurgery Clinic, "Cerebral embolism." https://www.minclinic.ru/cns_angio/cns_angio_eng/ cerebralnie_embolii_eng.html (accessed Sep. 21, 2019) (11 pages).
Mistry E.A. et al. "Blood Pressure after Endovascular Therapy for Ischemic Stroke (BEST): A Multicenter Prospective Cohort Study.," Stroke, vol. 50, No. 12, pp. 3449-3455, Dec. 2019.
Mistry E.A. et al. "Blood Pressure Variability and Neurologic Outcome After Endovascular Thrombectomy: A Secondary Analysis of the BEST Study.," Stroke, vol. 51, No. 2, pp. 511-518, Feb. 2020.
Mistry E.A. et al. "Mechanical Thrombectomy Outcomes With and Without Intravenous Thrombolysis in Stroke Patients," Stroke, vol. 48, No. 9, pp. 2450-2456, Sep. 2017.
Moodie T.B. et al. "Wave propagation and reflection in liquid filled distensible tube systems exhibiting dissipation and dispersion," Acta Mech., vol. 59, No. 3-4, pp. 139-155, 1986.
Mueller-Kronast N.H. et al., "Systematic evaluation of patients treated with neurothrombectomy devices for acute ischemic stroke primary results of the STRATIS registry," Stroke, vol. 48, No. 10, pp. 2760-2768, 2017.
Rucker D.C. et al. "Statics and Dynamics of Continuum Robots With General Tendon Routing and External Loading," IEEE Trans. Robot., vol. 27, No. 6, pp. 1033-1044, 2011.
Mynard, J. P. et al. "Measurement , Analysis and Interpretation of Pressure / Flow Waves in Blood Vessels," vol. 11, No. Aug., pp. 1-26, 2020.
Oglat, A.A et al. "A New Blood Mimicking Fluid Using Propylene Glycol and Their Properties for a Flow Phantom Test of Medical Doppler Ultrasound," Int. J. Chem., vol. 2, No. 5, pp. 220-231, 2017.
Orekhov A.L. et al. "Solving Cosserat Rod Models via Collocation and the Magnus Expansion," in IEEE/RSJ 2020 International Conference on Intelligent Robots and Systems, 2020, pp. 1-8.

(56) References Cited

OTHER PUBLICATIONS

Papanagiotou, P., et al. (2016). Endovascular reperfusion strategies for acute stroke. Cardiovascular Interventions, 9(4), 307-317.
Pile, J et al. "Detection of modiolar proximity through bipolar impedance measurements," Laryngoscope, vol. 127, No. 6, pp. 1413-1419, Jun. 2017.
Pile, J. et al. "Robot-assisted perception augmentation for online detection of insertion failure during cochlear implant surgery," Robotica, vol. 35, No. 07, pp. 1598-1615, Jul. 2017.
Poelma, C.. "Ultrasound imaging velocimetry: a review." Experiments in Fluids 58 (2017): 1-28.
Rai A. T. et al., "A population-based incidence of acute large vessel occlusions and thrombectomy eligible patients indicates significant potential for growth of endovascular stroke therapy in the USA," J. Neurointerv. Surg., vol. 9, No. 8, pp. 722-726, 2017.
Rai, A.T. et al. "Cerebrovascular geometry in the anterior circulation: An analysis of diameter, length and the vessel taper," J. Neurointerv. Surg., vol. 5, No. 4, pp. 371-375, 2013.
Raissi, M. et al. "Machine learning of linear differential equations using Gaussian processes," J. Comput. Phys., vol. 348, pp. 683-693, 2017.
Rajsic, S., et al. "Economic burden of stroke: a systematic review on post-stroke care." The European Journal of Health Economics 20 (2019): 107-134.
Renda, L. et al. "Discrete Cosserat Approach for Multi-Section Soft Robots Dynamics," p. 1, 2016.
Revellin, R. et al. "Extension of murray's law using a non-newtonian model of blood flow," Theor. Biol. Med. Model., vol. 6, No. 1, pp. 1-9, 2009.
Rone W.S. et al. "Continuum robot dynamics utilizing the principle of virtual power," IEEE Trans. Robot., vol. 30, No. 1, pp. 275-287, 2014.
Roy, R. et al. "Modeling and Estimation of Friction, Extension, and Coupling Effects in Multisegment Continuum Robots," IEEE/ASME Trans. Mechatronics, vol. 22, No. 2, pp. 909-920, Apr. 2017.
Samavat H. et al. "An ideal blood mimicking fluid for doppler ultrasound phantoms," J. Med. Phys., vol. 31, No. 4, p. 275, 2006.
San O. et al. "An improved model for reduced-order physiological fluid flows," Dec. 2012.
Sankar D.S. et al. "A non-Newtonian fluid flow model for blood flow through a catheterized artery-Steady flow," Appl. Math. Model., vol. 31, No. 9, pp. 1847-1864, 2007.
Sankar D.S. et al. "Pulsatile Flow of Two-Fluid Nonlinear Models for Blood Flow through Catheterized Arteries: A Comparative Study," Math. Probl. Eng., vol. 2010, pp. 1-21, 2010.
Santillan, A., et al. "Intraprocedural aneurysmal rupture during coil embolization of brain aneurysms: role of balloon-assisted coiling." American journal of neuroradiology 33.10 (2012): 2017-2021.
Saver, J. L., et al. "Stent-retriever thrombectomy after intravenous t-PA vs. t-PA alone in stroke." New England Journal of Medicine 372.24 (2015): 2285-2295.
European Patent Office. Extended European Search Report for Application No. 22825708.5, dated May 7, 2025 (11 pages).
Jin, X., et al. "A method for obtaining contact force between catheter tip and vascular wall in master-slave robotic system." 2020 IEEE International Conference on Mechatronics and Automation (ICMA). IEEE, 2020, 1597-1601.
Abolfazli, E. et al. "Dynamics of motion of a clot through an arterial bifurcation: A finite element analysis," Fluid Dyn. Res., vol. 46, No. 5, pp. 0-13, 2014.
Aoi, M. et al. "Modeling cerebral blood flow and regulation," Proc. 31st Annu. Int. Conf. IEEE Eng. Med. Biol. Soc. Eng. Futur. Biomed. EMBC 2009, pp. 5470-5473, 2009.
Benjamin E.J. et al., Heart Disease and Stroke Statistics'2017 Update: A Report from the American Heart Association, vol. 135, No. 10. 2017.
Berg J. et al. "Data-driven discovery of PDEs in complex datasets," J. Comput. Phys., vol. 384, pp. 239-252, 2019.
Berkhemer, O. A., et al. "A randomized trial of intraarterial treatment for acute ischemic stroke." New England Journal of Medicine 372.1 (2015): 11-20.
Bookstein F.L., "Principal warps: thin-plate splines and the decomposition of deformations," IEEE Trans. Pattern Anal. Mach. Intell., vol. 11, No. 6, pp. 567-585, Jun. 1989.
Brunton, S.L. et al. "Discovering governing equations from data by sparse identification of nonlinear dynamical systems," Proc. Natl. Acad. Sci. U. S. A., vol. 113, No. 15, pp. 3932-3937, 2016.
Brunton, S.L. et al. "Machine Learning for Fluid Mechanics," arXiv, 2019.
C. for D. C. & Prevention, "Stroke Facts." https://www.cdc.gov/stroke/facts.htm.
Campbell, BCV, et al. "Endovascular therapy for ischemic stroke with perfusion-imaging selection." New England Journal of Medicine 372.11 (2015): 1009-1018.
Cattafesta L.N. et al. "Actuators for active flow control," Annu. Rev. Fluid Mech., vol. 43, pp. 247-272, 2011.
Cesari, M., et al. "Frailty syndrome and skeletal muscle: results from the Invecchiare in Chianti study." The American journal of clinical nutrition 83.5 (2006): 1142-1148.
Chalasani, P. et al. "Concurrent nonparametric estimation of organ geometry and tissue stiffness using continuous adaptive palpation," in IEEE International Conference on Robotics and Automation, May 2016, pp. 4164-4171.
Chalasani, P. et al. "Preliminary Evaluation of an Online Estimation Method for Organ Geometry and Tissue Stiffness," IEEE Robot. Autom. Lett., vol. 3, No. 3, pp. 1816-1823, 2018.
Chang, S. et al. "Subject-Specific Computational Modeling of Evoked Rabbit Phonation," J. Biomech. Eng., vol. 138, No. 1, pp. 1-6, 2016.
Chen Y. et al. "A computational study of the three-dimensional fluid-structure interaction of aortic valve," J. Fluids Struct., vol. 80, pp. 332-349, 2018.
Chen Y. et al. "Pressure distribution over the leaflets and effect of bending stiffness on fluid-structure interaction of the aortic valve," J. Fluid Mech., vol. 883, 2020.
Chueh, J.Y. et al. "Mechanical characterization of thromboemboli in acute ischemic stroke and laboratory embolus analogs," Am. J. Neuroradiol., vol. 32, No. 7, pp. 1237-1244, 2011.
Chung B. et al. "CFD for Evaluation and Treatment Planning of Aneurysms: Review of Proposed Clinical Uses and Their Challenges," Ann. Biomed. Eng., vol. 43, No. 1, pp. 122-138, 2014.
Clinical Trials. "Trevo Aspiration Proximal Flow Control Registry, Stryker Neurovascular," 2019. Available online at https://clinicaltrials.gov/ct2/show/NCT03199404 (10 pages).
Cloft, H. J. et al. "Cerebral aneurysm perforations complicating therapy with Guglielmi detachable coils: a meta-analysis." American Journal of Neuroradiology 23.10 (2002): 1706-1709.
Dabiri J.O., "Optimal vortex formation as a unifying principle in biological propulsion," Annu. Rev. Fluid Mech., vol. 41, pp. 17-33, 2009.
Dash, R.K. et al. "Estimation of increased flow resistance in a narrow catheterized artery—a theoretical model," J. Biomech., vol. 29, No. 7, pp. 917-930, Jul. 1996.
De Castro-Afonso, L. H., et al. "The direct first pass aspiration technique in the treatment of acute ischemic stroke resulting from large vessel occlusions." Arquivos de Neuro-Psiquiatria 75.07 (2017): 412-418.
Denardo, S. J., et al. "Accuracy of Doppler catheter measurements: effect of inhomogeneous beam power distribution on mean and peak velocity." Journal of the American College of Cardiology 29.2 (1997): 283-292.
Di Martino E.S. et al., "Fluid-structure interaction within realistic three-dimensional models of the aneurysmatic aorta as a guidance to assess the risk of rupture of the aneurysm," Med. Eng. Phys., vol. 23, No. 9, pp. 647-655, 2001.
Donato G. et al. "Approximate Thin Plate Spline Mappings," in Computer Vision, 2002, pp. 21-31.
Duffy S. et al., "Novel methodology to replicate clot analogs with diverse composition in acute ischemic stroke," J. Neurointerv. Surg., vol. 9, No. 5, pp. 486-491, 2017.

(56) References Cited

OTHER PUBLICATIONS

Dumont, T. M., et al. "Aspiration thrombectomy in concert with stent thrombectomy." Journal of NeuroInterventional Surgery 6.4 (2014): e26-e26.
Duncan, E. R., et al. "Improved electrogram attenuation during ablation of paroxysmal atrial fibrillation with the Hansen robotic system." Pacing and clinical electrophysiology 35.6 (2012): 730-738.
Elijovich, L., et al. "Predictors and outcomes of intraprocedural rupture in patients treated for ruptured intracranial aneurysms: the CARAT study." Stroke 39.5 (2008): 1501-1506.
Elkenani, H., et al. (2017). Numerical investigation of pulse wave propagation in arteries using fluid structure interaction capabilities. Computational and Mathematical Methods in Medicine, 2017.
Feng, X., et al. "Procedural complications and factors influencing immediate angiographic results after endovascular treatment of small (< 5 mm) ruptured intracranial aneurysms." Journal of Stroke and Cerebrovascular Diseases 29.6 (2020): 104624.
Flores, J., et al. (2016). A novel analytical approach to pulsatile blood flow in the arterial network. Annals of biomedical engineering, 44, 3047-3068.
Ford M. D. et al., "PIV-measured versus CFD-predicted flow dynamics in anatomically realistic cerebral aneurysm models," J. Biomech. Eng., vol. 130, No. 2, pp. 1-9, 2008.
Froehler M.T. "Comparison of Vacuum Pressures and Forces Generated by Different Catheters and Pumps for Aspiration Thrombectomy in Acute Ischemic Stroke," Interv. Neurol., vol. 6, No. 3-4, pp. 199-206, 2017.
Froehler M.T. et al., "Interhospital Transfer Before Thrombectomy is Associated With Delayed Treatment and Worse Outcome in the STRATIS Registry (Systematic Evaluation of Patients Treated With Neurothrombectomy Devices for Acute Ischemic Stroke)," Circulation, vol. 136, No. 24, pp. 2311-2321, Dec. 2017.
Gao, E., et al. "Mathematical considerations for modeling cerebral blood flow autoregulation to systemic arterial pressure." American Journal of Physiology-Heart and Circulatory Physiology 274.3 (1998): H1023-H1031.
Goldman, R.E. et al. "Compliant Motion Control for Multisegment Continuum Robots With Actuation Force Sensing," IEEE Trans. Robot., vol. 30, No. 4, pp. 890-902, Aug. 2014.
Gounis, M.J. et al. "A thromboembolic model for the efficacy and safety evaluation of combined mechanical and pharmacologic revascularization strategies," J. Neurointerv. Surg., vol. 5, No. Suppl. 1, 2013.
Goyal, M., et al. "Endovascular thrombectomy after large-vessel ischaemic stroke: a meta-analysis of individual patient data from five randomised trials." The Lancet 387.10029 (2016): 1723-1731.
Goyal, M., et al. "Randomized assessment of rapid endovascular treatment of ischemic stroke." New England Journal of Medicine 372.11 (2015): 1019-1030.
Gralla J. et al. "A dedicated animal model for mechanical thrombectomy in acute stroke," Am. J. Neuroradiol., vol. 27, No. 6, pp. 1357-1361, 2006, [Online]. Available: http://www.ajnr.org/content/27/6/1357.short%5Cnhttp://www.ncbi.nlm.nih.gov/pubmed/16775297.
Haldar, S., et al. "Contact force sensing technology identifies sites of inadequate contact and reduces acute pulmonary vein reconnection: a prospective case control study." International journal of cardiology 168.2 (2013): 1160-1166.
Hasanzadeh, S. et al. "Model-based force estimation for intracardiac catheters." IEEE/ASME Transactions on Mechatronics 21.1 (2015): 154-162.
Holmlund P., "Computational Fluid Dynamic simulations of pulsatile flow in stenotic vessel models," Umea University, 2013.
Ihn, Y. K., et al. "Complications of endovascular treatment for intracranial aneurysms: management and prevention." Interventional Neuroradiology 24.3 (2018): 237-245.
International Preliminary Report on Patentability for Application No. PCT/US2022/033502 dated Dec. 14, 2023 (10 pages).
International Search Report and Written Opinion for Application No. PCT/US2022/033502 dated Oct. 26, 2022 (18 pages).
Isaksen J.G. et al., "Determination of wall tension in cerebral artery aneurysms by numerical simulation," Stroke, vol. 39, No. 12, pp. 3172-3178, 2008.
Schölkopf, B. et al. "New Support Vector Algorithms," Neural Comput., vol. 12, No. 5, pp. 1207-1245, May 2000.
Scott, S. et al. "Comparison of the elastic properties of human intracranial arteries and aneurysms.," Can. J. Physiol. Pharmacol., vol. 50, No. 4, pp. 328-332, 1972.
Siikonen T., "Computer Program Tmoc for Calculating of Pressure Transients in Fluid Filled Piping Networks," 1978, [Online]. Available: https://inis.iaea.org/collection/NCLCollectionStore/_Public/10/458/10458881.pdf?r=1&r=1.
Skalak R. et al. "Biofluid mechanics," Annu. Rev. Fluid Mech., vol. 21, pp. 167-204, 1989.
Szikora I. et al., "Impact of aneurysmal geometry on intraaneurysmal flow: A computerized flow simulation study," Neuroradiology, vol. 50, No. 5, pp. 411-421, 2008.
Tian, F.B. et al. "Fluid-structure interaction involving large deformations: 3D simulations and applications to biological systems," J. Comput. Phys., vol. 258, pp. 451-469, 2014.
Ujiie H. et al. "Effects of size and shape (aspect ratio) on the hemodynamics of saccular aneurysms: A possible index for surgical treatment of intracranial aneurysms," Neurosurgery, vol. 45, No. 1, pp. 119-130, 1999.
Van De Vosse, F.N. "Pulse wave propagation in the arterial tree," Annu. Rev. Fluid Mech., vol. 43, pp. 467-499, 2011.
Vargas, J., et al. "Experience with a direct aspiration first pass technique (ADAPT) for thrombectomy in distal cerebral artery occlusions causing acute ischemic stroke." World neurosurgery 99 (2017): 31-36.
Wang L. et al., "Force-Controlled Exploration for Updating Virtual Fixture Geometry in Model-Mediated Telemanipulation," J. Mech. Robot., vol. 9, No. 2, p. 021010, Mar. 2017.
Zhou J. et al. "The degree of nonlinearity and anisotropy of blood vessel elasticity," Proc. Natl. Acad. Sci. U. S. A., vol. 94, No. 26, pp. 14255-14260, 1997.
Weizsacker H.W et al. "Isotropy and anisotropy of the arterial wall," J. Biomech., vol. 21, No. 6, pp. 477-487, 1988.
Womersley, J. R. (1955). Method for the calculation of velocity, rate of flow and viscous drag in arteries when the pressure gradient is known. The Journal of physiology, 127(3), 553.
Xu K. et al. "An investigation of the intrinsic force sensing capabilities of continuum robots," IEEE Trans. Robot., vol. 24, No. 3, pp. 576-587, 2008.
Yasin R. et al. "Joint-level force sensing for indirect hybrid force/position control of continuum robots with friction," Int. J. Rob. Res., p. 027836492097972, Dec. 2020.
Yasin, R.M. et al. "Exploring Reflected Light Intensity to Estimate Depth of the Basal Turn in Cochlear Implant Surgery," in Hamlyn Symposium on Surgical Robotics, 2017, pp. 11-12.
Yoshida, T. et al. "Blood-mimicking fluid using glycols aqueous solution and their physical properties," Jpn. J. Appl. Phys., vol. 53, No. 7 Spec. Issue, pp. 3-8, 2014.
Yu, H. et al. "Calibration and Integration of B-Mode Optical Coherence Tomography for Assistive Control in Robotic Microsurgery," IEEE/ASME Trans. Mechatronics, vol. 21, No. 6, pp. 2613-2623, Dec. 2016.
Zaidat O.O. et al., "Impact of Balloon Guide Catheter Use on Clinical and Angiographic Outcomes in the STRATIS Stroke Thrombectomy Registry," Stroke, vol. 50, No. 3, pp. 697-704, Mar. 2019.
Zaidat, O. O., et al. "First pass effect: a new measure for stroke thrombectomy devices." Stroke 49.3 (2018): 660-666.
Zhang J. et al. "Design of Underactuated Steerable Electrode Arrays for Optimal Insertions," J. Mech. Robot., vol. 5, No. 1, p. 011008, Jan. 2013.

* cited by examiner

PERCEPTION FOR EFFECTIVE THROMBUS RETRIEVAL AND ANEURYSM EMBOLIZATION

CROSS-REFERENCE TO RELATED APPLICATIONS

This application is the U.S. national stage entry, under 35 U.S.C. § 371, of International Application Number PCT/US2022/033502, filed Jun. 14, 2022, which is a non-provisional of and claims the benefit of U.S. Provisional Patent Application No. 63/210,295, filed on Jun. 14, 2021, the entire contents of which are incorporated herein by reference.

BACKGROUND

During catheter-based treatments, surgeons are hampered by the limited sensory awareness of the microcatheters as they move through small, fragile, mobile vessels. While navigating a long (more than 1 meter) catheter, surgeons experience diminished haptic feedback. To navigate catheters, surgeons currently rely on static images of vessels superimposed on live fluoroscopy that shows the radio-opaque catheter tip. These perception deficits increase cognitive burden and diminish patient outcomes.

SUMMARY

To address the aforementioned needs, this disclosure provides a novel approach for indirect endovascular sensing that equips surgeons with two unprecedented capabilities: 1) estimate the distance between the catheter tip and a target (clot/aneurysm wall) and 2) evaluate the quality of the engagement of the catheter tip with a clot. The disclosed technology offers a low-cost rapidly deployable sensory solution, which is compatible with existing catheter technology and alleviates the above-described perception barriers in endovascular procedures such as ischemic stroke treatment and aneurysm embolization.

The present disclosure provides a new low-cost sensory solution that addresses needs in domains (e.g., neuroendovascular stroke treatment) where existing technologies such as ultrasound or integrated distal contact/force sensory solutions (e.g., strain gauges, fiber Bragg grating) stand in contrast to the need to achieve a design solution with a large working bore and a diameter smaller than 2 mm.

The disclosure describes several methods and embodiments for achieving sensory information for catheter-based interventions in general and specifically for endovascular ischemic stroke and aneurysm embolization procedures. The disclosure includes four key elements to its sensory function:

1. Estimation of distance from the catheter tip to a thrombus or aneurysm wall. This is achieved through the use of pulsatile vacuum excitation and sensing of the pressure at the proximal end of the catheter. A model of unobstructed flow in a catheter is used along with real-time sensory data about catheter insertion and sensed pressure to produce an estimate of the clot or aneurysm wall distance from the catheter tip. Further, use of the same model and sensory information to classify and inform the surgeon whether the catheter tip is in contact with a target.
2 Use of a pulsatile vacuum to draw a clot into an aspiration catheter tip.

3. Estimation of the quality of clot engagement based on a statistical model of pulsatile pressure profiles that include information regarding catheter motion, distance from clot, sensed pressure, and outcome of clot removal attempt. This statistical model is fused with intraoperative sensory information to produce an input into a forward prediction of clot engagement outcome.
4. Use of continuum mechanics of an extensible catheter to produce an informative model that produces a desired pulsatile axial tip motion of the catheter with the aim of using the catheter tip to burrow into a clot or to remove atherosclerosis plaque. This is achieved through modeling of the effects of pulsatile flow traction forces along the length of the catheter on the elastomeric and extensible catheter. This axial motion may be achieved purely through the judicious use of the elastomeric properties of a catheter at the end of a catheter tip.

Potential areas of application include:

1. Endovascular intervention in small vessels (smaller than 5 mm). For example: ischemic stroke, aneurysm treatment, arteriovenous malformations, arteriovenous fistulas.
2. Endovascular delivery of localized chemotherapy in targets accessible via small vasculature (e.g., ocular Neuroblastomas).
3. Endoluminal applications in Urology (e.g., uretroscopy) and Gynecology (e.g., fallopian tube intervention and localized delivery).
4. Atherosclerotic lesions in small vessels.
5. Industrial applications for catheter-like robots operating in turbid waters or in confined channels.

In one embodiment, the disclosure provides a method for determining the distance between a tip of a catheter and a target. The method includes applying flow and pressure excitation to a proximal end of the catheter, measuring a pressure change, with a pressure sensor in fluid communication with the catheter, at the proximal end of the catheter, the pressure change based on a cycle of applied proximal pressure excitation and advancement of the catheter toward the target, applying a machine learning model to the measured pressure change to determine the distance between the tip of the catheter and the target, and providing the distance between the tip of the catheter and the target to a user.

In another embodiment, the disclosure provides a method of classifying quality of engagement between a tip of a catheter and a target. The method includes applying flow and pressure excitation to a proximal end of the catheter, measuring a pressure signal, with a pressure sensor in fluid communication with the catheter, at the proximal end of the catheter, the pressure change based on a cycle of applied pressure excitation and advancement of the catheter toward the target, defining feature vectors for the pressure signal, computing changes in one of the feature vectors within two cycles of incremental axial motion of the catheter, applying a classification algorithm to the pressure signal to determine whether the tip of the catheter is in contact with the target, if the tip of the catheter is in contact with the target, applying vacuum excitation to promote catheter engagement with the target, and applying a regression method to predict quality of engagement of the tip of the catheter with the target.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Stroke Facts, Health Burden, and Situational Awareness Barriers

Figure 1:
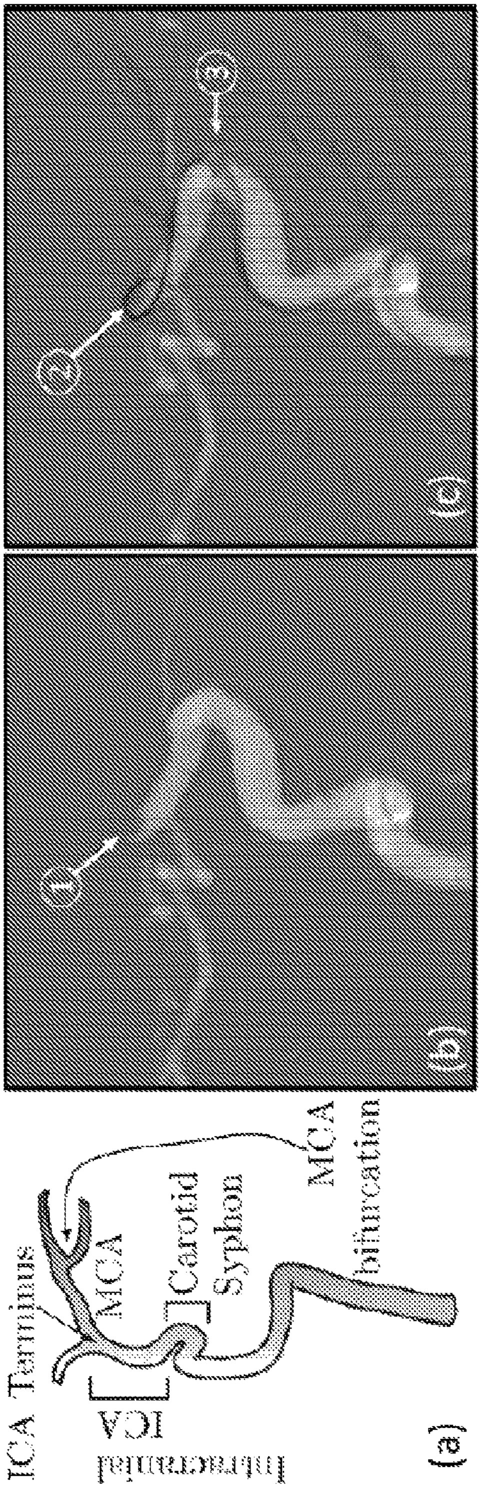
FIG. 1 illustrates (a) Relevant intracranial vasculature, (b) Roadmap of the left ICA showing clot position ①, (c) navigation roadmap used as a static background on which live fluoroscopy is overlaid: the microwire ② is used to navigate the tip of the aspiration catheter ③ to the clot site.

Stroke affects almost 795,000 patients per year and results in the fifth highest number of deaths in the U.S. (140,000/year) according to the Centers for Disease Control and Prevention, of which 87% are ischemic in nature. About 10% of these strokes (80,000/year) are due to large vessel occlusions (LVO) (blockage of one of the major arteries of the brain). FIG. 1 (at a) shows the key intracranial vessels. Based on enrollment in a recent study, 90% of thrombectomies arise from the intracranial ICA or proximal MCA. LVO results in more than 10,000 mechanical thrombectomy (MT) procedures/year in the U.S. alone. Despite their small percentage of overall strokes, strokes from LVO cause the largest portion of economic burden and death.

In 2015, MT became the treatment standard for acute LVO patients after several clinical trials showed its benefits. Patients treated with MT achieved recanalization rates up to 88% and had reduced disability rates at 90 days. The advantage of MT over intravenous thrombolysis with r-tPA alone (previous standard of care) was strong enough to justify ceasing patient enrollment in some of these clinical trials due to ethical concerns for the patients in the control group.

During MT procedures, neurointerventionalists inject a contrast agent through a guide catheter to obtain a digital subtraction angiogram (DSA) of the target vasculature. These images serve as a roadmap to navigate specialized thrombectomy catheters over a microcatheter and microwire to the LVO. FIG. 1 (at b) shows a roadmap of the left internal carotid artery (ICA). The clot position ① is deduced from the absence of contrast in a normally continuous vessel. This roadmap is used as a static background against which live fluoroscopy is overlaid, FIG. 1 (at c). The microwire ② and aspiration catheter ③ are radio-opaque and can be visualized in real time. The lack of force feedback at the tip of the catheter and the difficulty in discerning the true location of the clot relative to the catheter tip contribute to a situational awareness barrier reducing the success rate of MT.

The need for safe and fast treatment stands in direct contrast to the fact that surgeons currently rely on subjective measures (e.g., lack of blood return in the aspiration catheter) to infer engagement with the thrombus. These perception barriers contribute to a low success rate of 25% in achieving complete reperfusion from a single thrombectomy attempt-known as "first pass effect"-which is associated with significant improvement in clinical outcome. Each failed clot retrieval attempt reduces a patient's chances of recovery due to continued brain oxygen deprivation.

Importance of Thrombectomy and Rapid First-Pass Recanalization

Patient outcomes following endovascular treatment for acute ischemic stroke depend heavily on the ischemic time (time from onset of blockage to recanalization) and on the extent of recanalization of the cerebral vasculature. In a recent study by Kunz et al., based on data from the HERMES meta-analysis, it was shown that each 10 minute delay in ischemic time correlated with 40 days of added patient disability and $10,000 of added economic burden.

"First pass effect" is the achievement of complete revascularization from a single thrombectomy device pass. It has been associated with reduced ischemic time, lower mortality, reduced disability rate, and fewer procedural adverse events. However, with current thrombectomy techniques, first pass recanalization is achieved in only 25% of cases. Clot retrieval is abandoned after several time-consuming failed attempts when further benefits of restoring blood flow are outweighed by the surgical risk and the cumulative ischemic burden already suffered by the patient.

First-pass failure is partly due to sensory deficiencies hampering the surgeons' perception. These perception barriers are: 1) lack of simultaneous visualization of clot location and catheter tip, and 2) lack of sensory feedback about the level of engagement between the catheter tip and the clot. Surgeons currently rely on subjective measures (e.g., lack of blood return in the aspiration catheter) to infer engagement with the thrombus. After aspiration for 2-5 minutes with the clot engaged, the surgeon removes the catheter. If unsuccessful, the process of catheter preparation, navigation, and suction must be repeated.

Endovascular Embolization of Intracranial Aneurysms

In the United States, about 6.5 million people, are thought to harbor an unruptured intracranial aneurysm. Of those, approximately 30,000 people annually suffer from aneurysm rupture and 15% die before reaching a hospital. Worldwide, there are 500,000 annual deaths from ruptured aneurysms, with 50% of the victims younger than 50.

Figure 2:
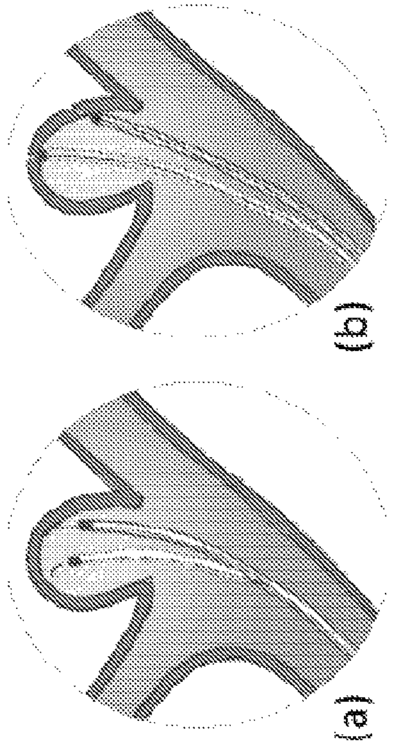
FIG. 2 illustrates a small aneurysm with a micro-catheter deployed (a) safe placement alternatives for microcatheter tip, (b) dangerous engagement between the catheter tip and aneurysm wall result in rupture upon guide-wire or coil delivery.

Endovascular coil embolization of ruptured and unruptured aneurysms is a common treatment in which the goal is to exclude the aneurysm from circulation, often by filling it with coils. Even when performed by experts, intraprocedural aneurysmal rupture (IAR) is a common and feared complication of endovascular treatment. This occurs in 1-11% of coiling procedures due to perforation of the aneurysm by the microwire, microcatheter, or coil. IAR causes a 4-fold increased risk of death or disability, consistent with 39% morbidity and 33% mortality rates. Extensive expertise and high clinical volume in endovascular aneurysm treatment has not been shown to affect the rate of IAR. Risk of mortality from IAR ranges as high as 40%. IAR occurs most commonly during treatment of ruptured aneurysms, aneurysms in the anterior communicating artery (likely from vessel tortuosity), and small aneurysms. These aneurysms require gentle placement of a microcatheter within the aneurysm sac in a position that allows for deployment of the coils (see FIG. 2).

During this process, the microcatheter is pushed over a microguidewire under live fluoroscopy, while using a static magnified roadmap of the intracranial vasculature to assist in navigation. This requires the patient to remain still and the operator to consider how the vasculature may shift as the catheters are manipulated within mobile vessels. With forward motion of the microcatheter, compressive elastic energy builds. As the microwire is removed, axial "spring-back" of the catheter tip can cause catheter malposition or aneurysm perforation.

Currently, perception of the microcatheter placement within the aneurysm is limited to the views captured by biplane angiography relative to the radio-opaque marker at the catheter tip. Resistance is inferred by observing the behavior of the wire or coil during its deployment and noting retraction of the microcatheter during forward pressure on the coil. When a balloon is simultaneously used to protect the parent vessel from which the aneurysm arises (balloon-assisted coil embolization), the operator's awareness of resistance is further limited because the microcatheter tip used to coil the aneurysm becomes fixed in place by the inflated balloon. The disclosure provides a sensory modality to enable the surgeon to measure the microcatheter's distance from the aneurysmal wall and ensure optimal positioning. This provides the interventionalist with an added sensory cue that would help avoid the often-fatal IAR.

Sensing of catheter tip forces has received extensive attention in the literature and point force sensing exists commercially for larger cardiac catheters. However, no tip contact or proximity sensing solutions currently can be used at the scale needed for intracranial procedures.

Ultrasonic sensing for flow velocimetry has been developed and explored for the past two decades. The presence of the ultrasonic piezoelectric elements at the catheter tip prevents miniaturization while retaining a hollow and flexible tip. Such catheters have been used for cardiac applications. Miniature IVUS ablation and imaging catheters (e.g., Boston Scientific's Ultra-ICE™) lack the necessary tip flexibility and a working bore.

The disclosure is focused on indirect measures for estimating target (e.g., a clot) engagement and proximity to the target (e.g., a clot or aneurysm wall. Within the area of fluid mechanics, Womersley's seminal work on pulsatile flow in a straight pipe has been followed by numerous works focused on pulsatile flow in soft arteries and works on pressure wave propagation in pipes and arteries. Also, many works focused on flow modeling within the cerebral network.

The flow and pressure (e.g., vacuum) excitation-based sensing technique disclosed herein presents a scenario that is different from either the natural or the engineered situations in previous publications. Unlike the natural arterial blood flow, in the present problem the pulsatile jet produced by the syringe through the catheter tip is reminiscent of a zero-net-mass-flux oscillatory jet, or synthetic jet, in many flow control applications. However, the present jet is confined by a flexible vessel (the artery) and is thus unlike most of the synthetic jets. The presence of the blood clot or the aneurysm adds complexities to the flow problem, which does not lend itself to a simple analytical solution. Although there have been many studies of the blood flow through an aneurysm, including fluid-structure interaction (FSI), they primarily focused on blood flow in the natural direction, rather than the opposite direction created by vacuum here. Therefore, disclosed herein is a computational fluid dynamics (CFD) model to solve the fluid-structure interaction caused by catheter excitation, and from the CFD results, machine learning is employed to generate convenient function expressions of the pressure change in relation to the catheter-clot/aneurysm distance that can later be used for the sensing purpose.

As noted above, there exist current limitations of the state-of-the-art in perception for stroke and aneurysm embolization: (1) Surgeons currently lack the ability to sense the position of a catheter tip relative to the flexible and delicate vasculature. This results in reliance on static overlay images of vascular anatomy which does not reflect the true state of the vasculature and contributes to a heavy cognitive burden and a high rate of aneurysm ruptures. (2) In stroke, surgeons must resort to subjective measures to guess when a clot is sufficiently engaged for retrieval. There have been no prior works on quantifying the quality of catheter tip engagement with a clot. This limitation contributes to a low first-pass effect and poor clinical outcomes. (3) None of the catheters or prior works address sensing at the scale needed for neurointervention while preserving a working bore and a very flexible tip as required for safe intracranial navigation.

The disclosure offers a transformative low-cost sensory technology that can help overcome much of the aforementioned scientific gaps and clinical needs. With the above-mentioned technological and scientific advancements falling short of providing sensory feedback, a new approach is needed. A pragmatic approach is disclosed to achieve situational awareness that can help neuroendovascular surgeons. Although previous works on pulsed flow provide a theoretical foundation to understanding the mechanics of the problem, they cannot be directly applied here since a pulsed flow in a very small volume containing the catheter and the portion of artery up to the clot and its connecting network is considered. Furthermore, most works focus on modeling the cardiac arterial network and there are limited works on modeling pulsed flow within the cerebral vascular network and even fewer works considering the presence of a catheter. Therefore, disclosed herein are CFD models that also consider the fluid-structure interaction and to augment these models by casting the problem of distance measurement to a target as an identification problem and by leveraging machine learning regression methods.

Figure 3:
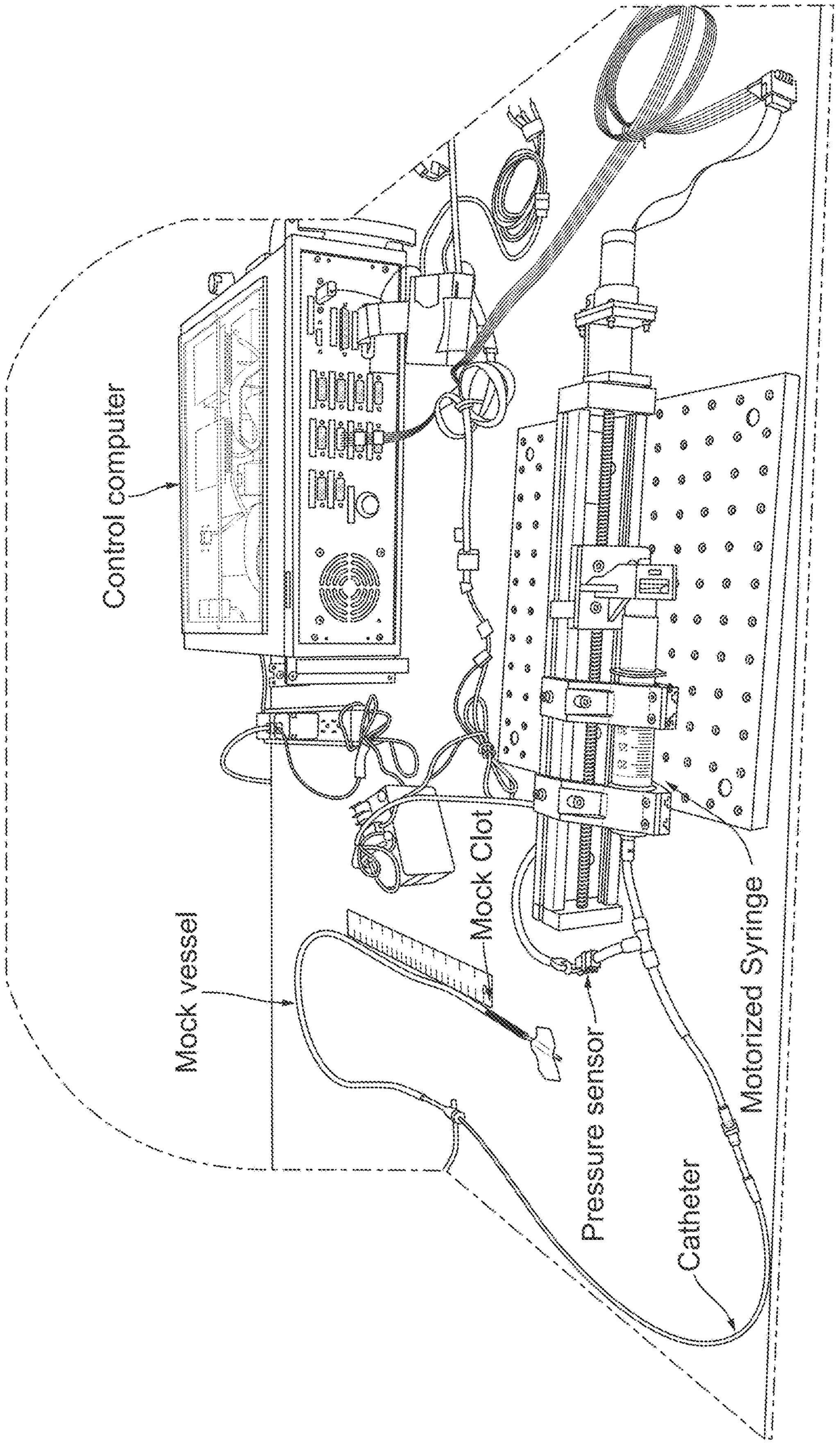
FIG. 3 illustrates an experimental setup of a system for providing assistive perception for effective thrombus retrieval and aneurysm embolization according to an embodiment of the present disclosure.

FIG. 3 illustrates a system 10 fabricated to test the feasibility of the approach. The system 10 includes a syringe 14 (e.g., 60 ml) coupled to a standard aspiration catheter 18 (e.g., AXS Catalyst 6, Stryker Neurovascular), which was inserted into a mock vasculature 22 filled with saline and capped with a mock target 26 (e.g., a clot). In an example, the initial experiments included Tygon tubes as mock vasculature having an inner diameter of 3.2 mm and an outer diameter of 6.3 mm. These tubes allowed visualization of the catheter tip motion and its distance from the target 26.

Figure 4:
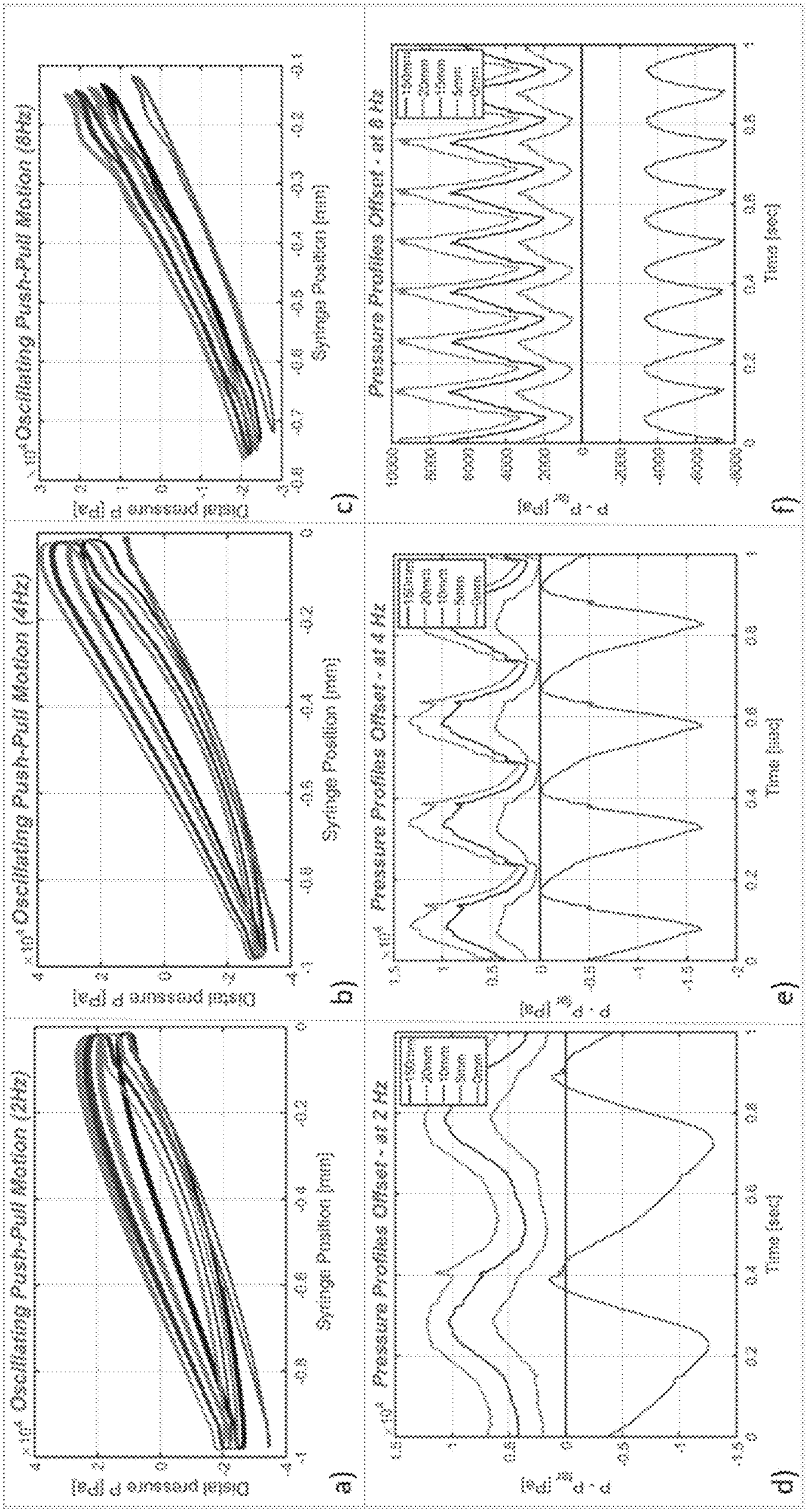
FIG. 4 illustrates data collected from pressure excitation. (a-c) The relationship between the pressure at the distal end of the catheter and the syringe position in millimeters for a single trial at 2 Hz, 4 Hz, and 8 Hz, respectively. (d-f) The pressure at the distal end of the catheter at each distance compared to the pressure at 150 mm over time for 2 Hz, 4 Hz, and 8 Hz.
Figure 5:
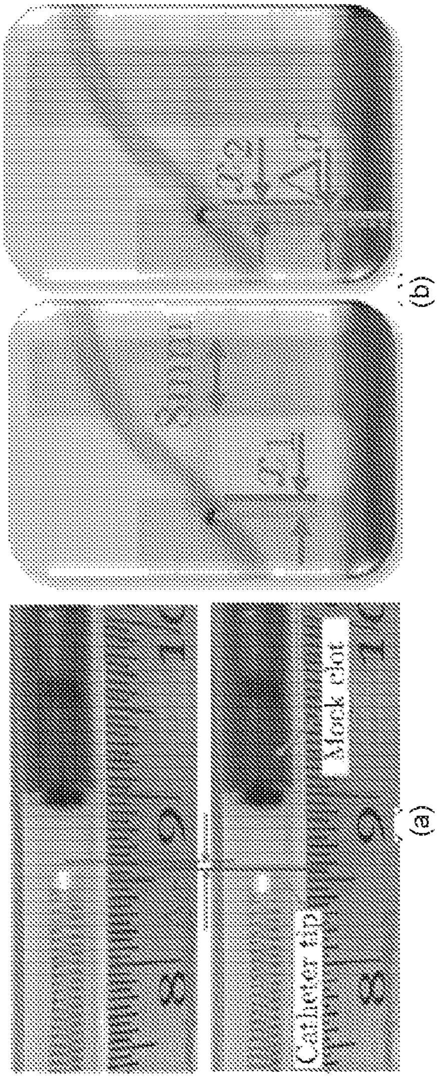
FIG. 5 illustrates (a) two snapshots of the video showing the catheter tip axial oscillation, (b) segmentation snapshots of catheter tip from fluoroscopy images show the catheter tip oscillation.

The experiments also tested feasibility in very soft latex tubing as mock vasculature representing the other end of the spectrum of vessel wall softness. A motion excitation was applied to the piston of the syringe 14 using a slider-crank mechanism or a linear actuator. The catheter tip was placed at several distances from the mock target 26 and a digital vacuum pressure sensor 32 was placed near the syringe 14 to measure the induced cyclic vacuum as a function of syringe stroke. Using a motion excitation of 0.5 mm at 2 Hz, 4 Hz, and 8 Hz, the results obtained are shown in FIG. 4 (at a, b, and c). The pressure at the distal end of the catheter at each distance compared to the pressure at 150 mm over time for 2 Hz, 4 Hz, and 8 Hz is shown in FIG. 4 (at d, e, and f). In addition, it was observed that the vacuum excitation induces axial shrinkage and relaxation in the aspiration catheter 18 as shown in FIG. 5 (at a). To verify that such small catheter tip motion may be discernible, the catheter tip was moved in a cyclic motion of approximately ±0.2 mm while observing the catheter tip using a bi-plane fluoroscopy machine. FIG. 5 (at b) verifies the ability of the image segmentation and catheter tip tracking algorithm to discern this small motion.

FIG. 4 (at a, b, and c) demonstrates that the sensed vacuum is cyclic and mostly repeatable. Also, the vacuum gradient with respect to piston pull is dependent on the distance of the catheter tip from the target. These results suggest that an interpolation map relating the catheter tip distance from the target may be obtained as a function of vacuum pressure, its gradient with respect to piston motion, and the change in the gradient as a function of catheter advancement. FIG. 5 (at a and b) also show that catheter tip pulsation induced by shear flow stresses on the catheter can be observed using fluoroscopy and be used as a second source of information for the sensing approach for detecting clot proximity and engagement.

Figure 6:
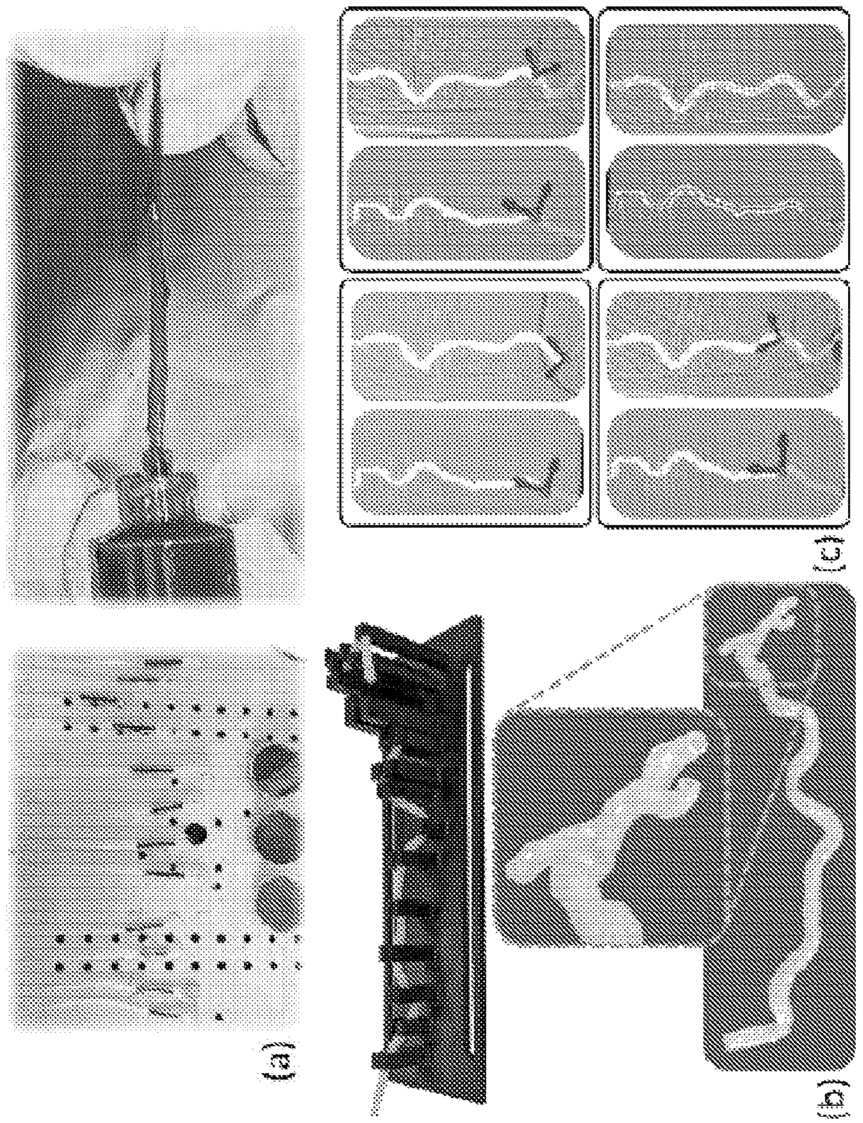
FIG. 6 illustrates (a) swine blood clots prepared at different consistencies, (b) two vessel models using 3D printing and silicone rubber (top) and using dipping (bottom), (c) bi-plane fluoroscopy image segmentation and tracking of catheter tip.

This approach was validated to create blood clots from swine blood as shown in FIG. 6 (at a) and used segmented CT scans of a human ICA to generate a 3D model of the vasculature. FIG. 6 (at b) shows two out of four fabrication approaches successfully developed in-house. The top of FIG. 6 (at b) shows a hybrid model using a 3D print to constrain a latex sheath that serves as a flexible mock artery. The bottom portion of FIG. 6 (at b) shows an ICA model fabricated using sacrificial wax printing followed by silicone dipping.

A digital subtraction angiogram and SmartMask of the phantom vasculature were obtained by using a contrast agent (e.g., Omni 200) under bi-plane fluoroscopy. Image segmentation algorithms were developed to segment and track a catheter. The segmentation and tracking were achieved at 20 Hz for the vasculature, and 10 Hz for the catheter. Higher segmentation rates (e.g., better than 60 Hz) are achievable when porting Matlab to C++. FIG. 6 (at c) shows sample segmentation and tracking results.

The disclosure provides a method for reliably sensing the distance of a catheter tip from a target (e.g., clot/aneurysm wall) and for classifying the quality of engagement with a target (e.g., a clot). The modeling and experimental validation focuses on solving these two problems for targets positioned along the intracranial ICA and MCA as depicted in FIG. 1 (at a). The rationale for this focus stems from the fact that more than 90% of the LVO ischemic strokes are observed in these vascular segments. For the aneurysm wall detection, the focus is on an aneurysm at the MCA bifurcation in the ex-vivo experimental validation phase. This location was selected as the test example since aneurysms commonly occur at blood vessel branch points like the MCA bifurcation.

The accuracy of target distance/aneurysm wall measurement was validated in ex-vivo and animal models and to establish the utility of such sensory information in a user study. Since the target locations and the vessel diameters vary between subjects, a three-phase approach was defined: Phase 1 (Nominal geometry): focus was on CFD modeling and calibration for a vessel geometry corresponding with the 95% confidence intervals of vessel diameters; Phase 2 (Sampled geometry library): focus was on CFD modeling and calibration based on a library of sample vessel geometries from CT scans; and Phase 3 (Novel geometry): focus was on validation in arbitrary vessel geometries that have not been included in the model calibration set. These phases were completed on ex-vivo models before the planned animal validation.

Figure 7:
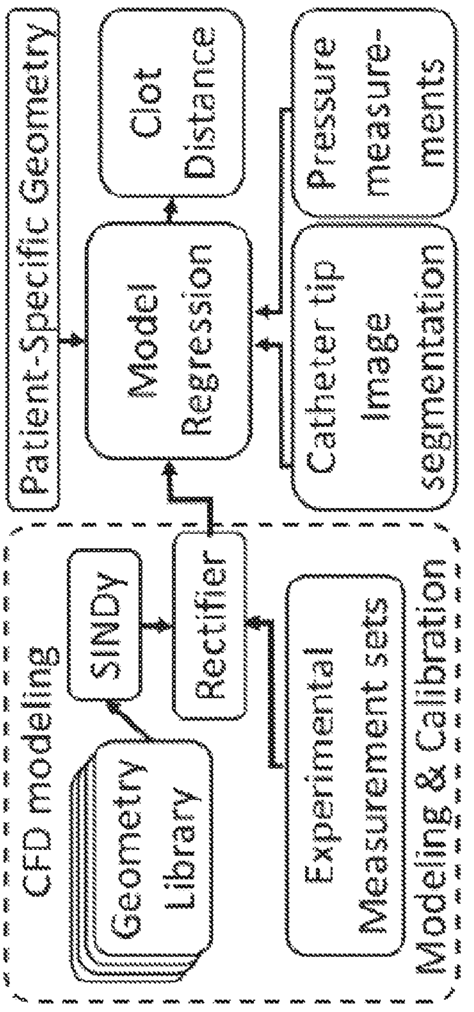
FIG. 7 illustrates an overview of the disclosed approach for distance sensing.

FIG. 7 provides a visual overview of the three-phase approach. Phase 1 serves the purpose of establishing the CFD modeling and experimental calibration process. Phase 2 allows us to use several patient-specific vessel geometries and corresponding phantom models to generate a library of calibrated CFD models. For each model, a Gaussian process regression curve represented the change in a state vector (feature vector) that included the sensed pressure as a function of catheter tip distance from the target. For a given patient vessel geometry, these models were interpolated and used to produce a distance measurement. Phase 3 serves for experimentally validating and refining this process using a novel set of vessel geometry not included in Phase 2.

Figure 8:
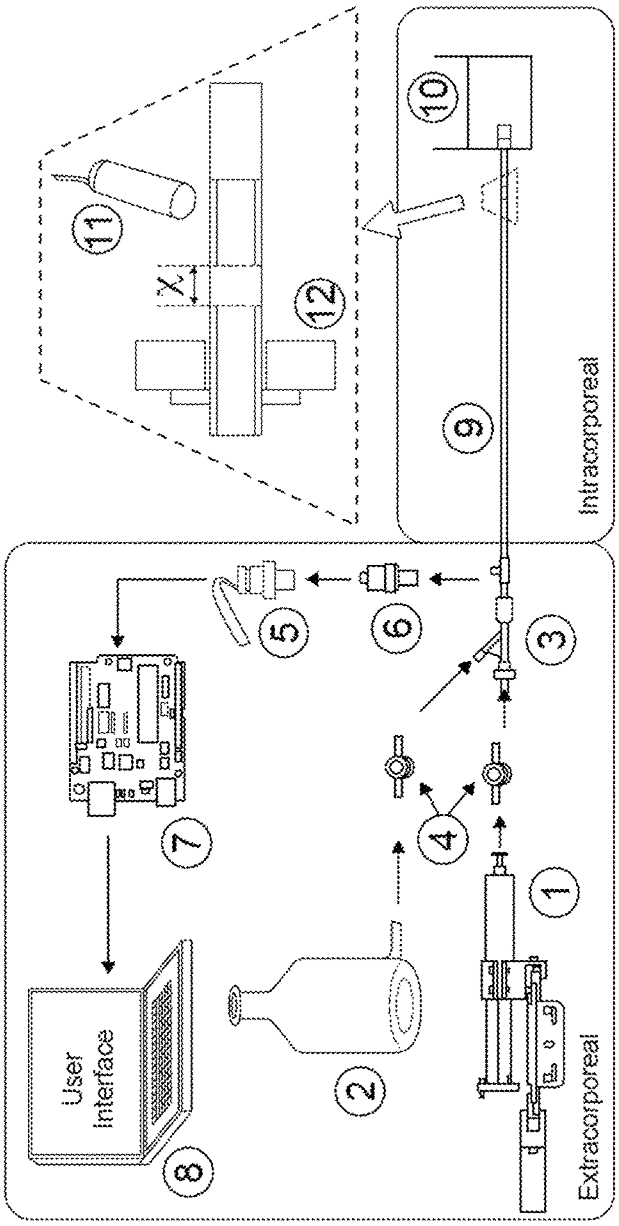
FIG. 8 illustrates an experimental setup for investigating proximity and clot/aneurysm wall engagement.

FIG. 8 shows the ex-vivo experimental setup. The mock vasculature was filled with blood mimicking fluids (BMFs) (e.g., Shelley Medical Imaging Technologies) to reduce the biological risk. BMFs have been shown to replicate the flow properties of blood. To generate pulsatile vacuum, a vacuum syringe, such as the VacLok syringe (100 in FIG. 8) commonly used for manual aspiration thrombectomy was oscillated. The syringe 100 was filled with saline and oscillated using closed-loop control of a voice-coil actuator (e.g., Moticont VCDS-025-038-02-B2-30). The syringe 100 was connected to a hemostasis valve 104 which has two stopcock valves 108 on input branches. One of the branches connected to a BMF reservoir 112 and the other to the syringe 100. The reservoir 112 was used to fill the aspiration catheter 118 at the priming stage when the reservoir stopcock was subsequently closed. The output of the hemostasis valve was connected to a T-connector 122, which also connected to both the vacuum sensor 126 and the proximal end of the catheter 118. A check valve 130 prevented backflow between the vacuum sensor 126 and the syringe-catheter subsystem. Prior works have experimentally determined that the vacuum level applied during aspiration thrombectomy ranges between −27 to −23 inHg. We therefore used a pressure sensor ranging from −30 to 30 inHg (e.g., Honeywell 26PCCFB2G). The vacuum was read through an analog input to a sensory and data logging computer 134 (e.g., PC/104 control computer) and sent to a graphical user interface via User Datagram Protocol (UDP). The syringe motion and catheter insertion motion were measured using a linear encoder/potentiometer 136. During the ex-vivo model identification experiments, the apparatus included a camera 138 to monitor the engagement aspiration catheter and the clot and pressure sensors close to the clot and close to the syringe. A standard aspiration catheter (e.g., REACT-68, ID 1.73 mm) was used. We defined the signed distance between the distal tip of the catheter 118 and the proximal end 142 of the clot x as the metric for catheter-clot engagement. The camera 138 recorded time-stamped images of the clot, catheter distal tip, and a ruler by interfacing with the control computer 134 for data-logging, and x was segmented.

Vasculature and Clot Models for ex-vivo bench-top studies. In the preliminary stage of the ex-vivo investigation, straight tubing was used as the vascular models. This tubing ranged in hardness from Tygon PVC tubing (ID 3.175 mm) to rubber latex (ID 3.048 mm), and had geometric properties that match the diameter (2-5 mm) of large intracranial vessels (ICA, MCA) and the length from the femoral artery to the site of occlusion in the ICA (about 1 meter). These straight models were used initially to minimize the frictional effects that can mask the traction force experienced by the target.

During Phase 1 and Phase 2 of this study, these straight models were replaced with phantom models matching the geometry of the ICA from CT scans (as in FIG. 6 (at b)). In Phase 1, the results used were described in E. A. Mistry et al., "Blood Pressure after Endovascular Therapy for Ischemic Stroke (BEST): A Multicenter Prospective Cohort Study," Stroke, vol. 50, no. 12, pp. 3449-3455 December 2019, doi: 10.1161/STROKEAHA.119.026889, reporting the 95% confidence intervals of diameters related to the vasculature shown FIG. 1 (at a). In Phase 2, data was collected on phantom models based on 30 patient-specific CT scans.

All of these vessel models were extended to include the aortic arch (and its branches) and the femoral artery. A commercial model (e.g., from Elastrat) may be well-suited for this application as well. It is a transparent soft silicone model that is continuous from femoral artery up to the intracerebral circulation, including thoracic and abdominal aorta, aortic arch, great vessels in the neck, and intracranial ACA and MCA with intact circle of Willis. This model also provides a closed system with a fluid pump to mimic vascular circulation and allows vascular catheter access.

A mock target (e.g., a clot) was lodged at the distal end of the mock vasculature to simulate vessel occlusion. The use of coagulated swine blood as a clot was previously investigated as shown in FIG. 6 (at a). The repeatability of the clot fabrication process was determined by characterizing adhesion forces between the mock clot and the mock vasculature. This characterization experiment was carried out on 50 clots of equal length fabricated within Tygon tubing and the clot retrieval force was measured using a load cell holding the mock vasculature.

CFD Models and Verification/Calibration of These Models. The computational fluid dynamics (CFD) models are a way to generate a large data set exceeding the 30 phantom models upon which experiments were conducted. These models can be run with different geometries and model parameters to generate synthetic data after proper model calibration in Phase 1 and 2. However, these models are not suitable for real-time applications, so we planned to proceed with an intelligent statistical regression model as shown in FIG. 7.

Figure 9:
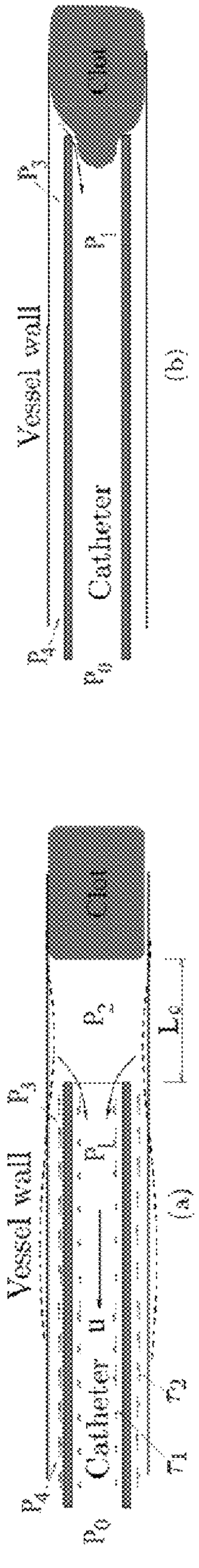
FIG. 9 illustrates a schematic of CFD models for distance sensing (a) and clot engagement (b), where wall deformation in A and clot deformation in B are shown. The red arrows in (a) indicate the flow-induced shear stresses on the catheter wall.
Figure 10:
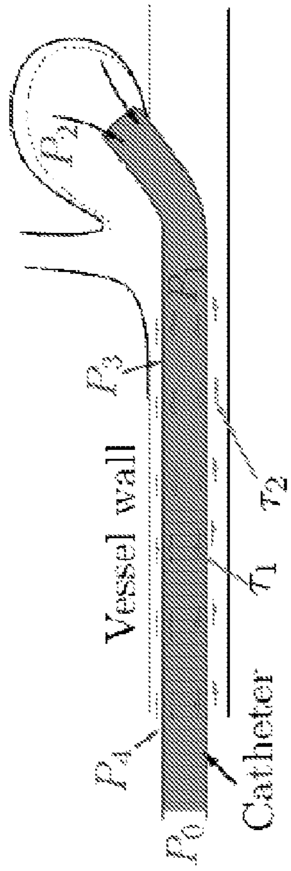
FIG. 10 illustrates a schematic of CFD models for distance sensing of an aneurysm, where the wall deformation is shown. The red arrows indicate the shear stresses due to flow on the interior and exterior surfaces of the catheter.

Pressure transmission under pulsatile flow excitation in a catheter within a flexible blood vessel. During vacuum excitation, the flow path included the syringe, the interior of the catheter, and the region between the catheter tip and the target, and the gap between the catheter and the vessel wall (FIG. 9 (at a)). While the core flow inside the catheter and the annular flow in the catheter-vessel gap was approximated by fully-developed laminar flow in a pipe and flow in a concentric annulus, respectively, the end effect due to the presence of the clot and the effect of wall compliance complicated the problem and warranted a numerical solution. A CFD model was used for FSI of the catheter tip as shown in FIG. 9 (at a), where the focus was on the pulsatile jet fluid dynamics in the region between the catheter tip and the clot. Given the syringe movement (amplitude and frequency), the distance from the tip to the clot, $L_c$, and the geometrical/material parameters, the CFD model was coupled with the core flow model and the annular flow model to determine the instantaneous pressure at a few key locations: $P_0$ at the base (near syringe), $P_1$ inside the catheter near the tip, $P_2$ between the tip and the clot, Pa outside the catheter near the tip, and $P_4$ outside catheter away from the tip. After model validation, the CFD model was used to perform a systematic parameter study to determine the pressure drop around the catheter tip, $P_3$-$P_1$; then the CFD results were used as training data for a machine learning model to generate a function expression of this pressure drop. Combined with the theoretical models of pressure drops of $P_1$-$P_0$ and $P_4$-$P_3$, the function expression of the overall pressure drop, $P_4$-$P_0$ in the system was obtained. The overall pressure drop function was then used to 1) determine the optimal excitation amplitude and frequency of the syringe, and 2) determine the tip-clot distance in the sensing process.

Since the Reynolds number of the flow is relatively small (100 or less), turbulence was not expected. However, vortices near the catheter tip due to jet pulsatility affect the local pressure around the tip. A time-dependent FSI model was developed for the pulsatile jet that included the jet flow, wall compliance of the elastic vessel, and the axial oscillation of the catheter tip. The wall compliance allows the vessel wall to deform inward under the vacuum pressure, thus dynamically changing the fluid volume and forming a flexible reservoir. The catheter also experienced an extension/compression oscillation of around 0.5 mm at the tip due to the shear stresses exerted by the flow on the tube's interior and exterior surfaces (FIG. 9 (at a)). This oscillation affected the jet dynamics and pressure drop when the catheter was only a few mm away from the clot. In the FSI model, the vessel wall deformation was solved concurrently using a finite element model (FEM) of the anisotropic artery. To include catheter tip oscillation, the models of the core flow and the annular flow inside/outside the catheter were used to describe the shear stresses by these flows, and to couple them with the catheter's mechanics model to be derived and experimentally calibrated. These coupled equations governed the elastic mechanism for the catheter tip dynamics.

Model validation. To validate the CFD model, a pressure transducer needle (e.g., From Galetech) will be inserted into the vessel near the catheter tip to monitor the instantaneous pressure $P_2$. For the validation purpose, we will compare the pressure at the base $P_0$, pressure at the tip $P_2$, and the tip oscillation obtained from the numerical simulation with those obtained from the in vitro experiment. The comparison will be done for a large tip-clot distance (~20 mm), a medium distance (3 to 5 mm), and a close distance (~1 mm).

Parameter study with the CFD model. After model validation, a systematic study of the governing parameters will be performed, including geometrical parameters such as the catheter diameter d, vessel diameter $d_c$, tip-clot distance, $L_c$, material parameters such as the dynamic elasticity of the anisotropic vessel wall, and excitation parameters such as the syringe oscillation frequency and magnitude, f and A. These parameters will be grouped into non-dimensional terms, e.g., the jet Reynolds number, $$Re = \frac{\rho u d}{\mu},$$

the Strouhal number, $$St = \frac{fd}{u},$$

the distance-to-diameter ratio, $L_c/d$, and the normalized wall elasticity, $E/\rho u^2$, where $\rho$ and $\mu$ are the blood density and viscosity, respectively, and u is the average jet velocity (~40 mm/s). These parameters will be varied according to the physiological condition of the artery and the design constraints of the catheter. For the simulation, since the deformation of the vessel wall and displacement of the catheter tip are relatively small, COMSOL Multiphysics or ANSYS FLUENT and their moving-mesh capability will be used to solve the FSI problem.

Pressure transmission and reflection under pulsatile flow excitation near a soft aneurysm wall. It has been known that the presence of an aneurysm may significantly affect the local flow pattern in the blood vessel. However, how the flow pattern, the aneurysm deformation and the pressure drop in the flow as affected under the proposed catheter excitation, are yet unknown. A CFD model will be developed to solve this FSI problem of (FIG. 8) and determine the pressure drop around the tip, $P_3$-$P_1$, in relation to the excitation parameters and the tip-aneurysm wall distance. Both the vessel and aneurysm walls will be modeled as elastic structures, whose nonlinear properties are available. Like the CFD model in clot sensing, the core flow inside the catheter and the annular flow between catheter and the vessel will be described using well-established theoretical equations and will be incorporated into the CFD model so that the overall pressure drop, $P_4$-$P_0$, will also be determined. For model validation, the base pressure $P_0$, near-tip pressure $P_2$, as well as the aneurysm wall deformation will be compared with those obtained in the in vitro experiment. COMSOL Multiphysics or ANSYS FLUENT will be used for such simulations. However, in case that the aneurysm deformation becomes too large and causes challenges to the numerical simulation, we will resort to our in-house code that is based on an immersed-boundary method and is specially designed to handle FSI problems involving complex geometries and large deformations of biological tissues. In the past, this code has been used to successfully model the FSI of heart valves and vocal fold vibration.

After model validation, a systematic study of the CFD simulations will be performed to study the effects of the parameters including the tip-wall distance, Reynolds number, Strouhal number, vessel/aneurysm wall compliance as defined in the preceding section for clot sensing. The geometry of the MCA bifurcation, including the branch diameters and aneurysm size, will also be varied in the parameter study. The CFD results will be used as the training data in the machine learning package, SINDy, to generate the function expression of the pressure drop around the tip in terms of non-dimensional parameters. In the actual sensing procedure, the size and wall thickness of the aneurysm, as well as the geometry of bifurcation will be obtained from the pre-operative scan. With those data, the function relationship between the base pressure and tip-wall distance will be used to 1) optimize the excitation parameters and 2) perform the aneurysm wall sensing task.

Modeling clot engagement and flow into the catheter after pulsatile vacuum. Once the catheter tip is in engagement with the blood clot, the clot may deform and partially or fully enter the catheter tube to block the flow (FIG. 9 (at b)). The clot's deformation depends on the clot's elasticity and the vacuum pressure inside the catheter tip, $P_1$, which is a result of the syringe activation but is affected by presence of leaking through any catheter-clot gap. The CFD model will be developed to simulate the deformation of the clot during the engagement and calculate the pressure inside the catheter tip, $P_1$, as well as the vacuum force applied to the clot, for any assumed leak opening, and the simulation results will be used in the machine learning process to assess the quality of engagement (i.e., the extent of the clot entering the catheter).

The CFD model will include an FEM model of the blood clot, a simplified leaking channel whose length depends on the entrance length of the clot, as well as the theoretical models of the core flow and the annular flow inside/outside the catheter. The elastic properties of the clot will be taken from J. Y. Chueh, A. K. Wakhloo, G. H. Hendricks, C. F. Silva, J. P. Weaver, and M. J. Gounis, "Mechanical characterization of thromboemboli in acute ischemic stroke and laboratory embolus analogs," Am. J. Neuroradiol., vol. 32, no. 7, pp. 1237-1244, 2011, doi: 10.3174/ajnr.A2485 and W. Merritt et al., "Quantifying the mechanical and histological properties of thrombus analog made from human blood for the creation of synthetic thrombus for thrombectomy device testing," J. Neurointerv. Surg., vol. 10, no. 12, pp. 1168-1173, 2018, doi: 10.1136/neurintsurg-2017-013675. During engagement, the blood may experience high shear locally inside a small gap. If that is the case, a non-Newtonian model for the blood will be adopted. For model validation, the pressure at the base, $P_0$, and the clot deformation will be compared with those obtained from the in vitro experiment. After model validation, a systematic study of engagement for the governing parameters including the vessel and catheter diameters, the clot size, and the size of the leaking gap will be performed. The results will be used in machine training to generate a function expression of the extent of deformation in relation to the pressure at the base and the syringe displacement, and this function expression will be used in the catheter procedure to assess engagement quality.

Clot Proximity Sensing Ex-vivo experiments and model update/calibration (Phase 1 and 2). The CFD models will provide the expected pressure reading at the proximal end of the catheter as a function of several parameters including tip proximity to the clot. Oscillatory vacuum aspiration will be used within a range consistent with the reported literature and the catheter will be advanced at a fixed rate using a motor-controlled linear stage. Vacuum levels will be recorded at the pull-phase of the syringe's cyclic motion and the distance from the clot will be obtained from image segmentation and measurement of catheter advancement.

Early experiments in Phase 1 will focus on system parameter identification of the catheter pressure transmission with the aim of maximizing the sensitivity of the change in sensed pressure $P_0$ to a change in the distance of the catheter tip to the clot $L_c$ (FIG. 9 (at a)). While advancing the catheter, the voice coil actuator will be pulsed and the pressures $P_0$ and $P_2$ will be measured and recorded. This process will be repeated for a spectrum of frequencies and syringe amplitudes to determine the regime that maximizes sensitivity $$\frac{dP_0}{dL_c}.$$

The dynamic head-loss will be identified by placing the catheter in an open tank filled with BMF. Using the expected flow model based on the syringe stroke and frequency, the Darcy-Weisbach friction coefficient will be determined for laminar flow and calibrate the CFD model by collecting data at several distances from the clot and producing regression models to allow interpolation of the experimental data for the given anatomy library in Phase 2, FIG. 7. By repeating the CFD simulations for each sample anatomy for sample locations along the arc-length of the vasculature and for diameter variations, an expanded data set will be produced that serves as an input to a process of sparse model reduction (SINDy, in FIG. 7). Using this model, the Bernstein polynomial series regression will be initially used on the SINDy model output at these arc-length locations. A Gaussian Process Regression (GPR) will also be used to encode the uncertainty in the data based on the diameter variations. This step will be followed by experimental model rectification for unmodeled effects (Rectifier, in FIG. 7).

During Phase 1 and Phase 2 experiments, vacuum data and the distance of the catheter tip from the clot, the speed of motion of the syringe piston, the rate of change of the pressure, and the rate of insertion of the catheter will be collected. These sensory variables will serve the purpose of auto-labeling of data sets as belonging to pre-clot engagement versus post-clot engagement phases. The conclusion of Phase 1 experiments will yield a statistical model (distribution) describing the expected change in pressure $$\frac{dP_0}{dL_c}$$

and the sensed pressure at a given excitation phase as a function of distance from the clot and this will correspond with the nominal vasculature model with its assumed range of diameter variations. At the end of Phase 2 experiments, similar statistical models will be derived for each patient-specific (CT-based) phantom vasculature.

For Phase 3, these rectified models will be used for each anatomical variation to generate a regression map so we can predict the CFD model output (L_c in FIG. 8 (at a)) for any arc-length location of the catheter tip, a given location of the clot, and for a novel vessel geometry.

With reference to FIG. 7, each of the steps are described in detail. MODEL REDUCTION. After a nominal CFD model has been obtained, the first step is model reduction via a sparse polynomial representation. Using the output from the nominal CFD model simulations as training data for a machine learning process, an explicit expression of the pressure drop near the catheter tip is generated as a function of the non-dimensional parameters including Re, St, $L_c/d$, $d_c/d$, normalized wall thickness h/d, and compliance $E/\rho u^2$. In fluid mechanics, many machine learning techniques have been developed to identify the governing equation directly from data. The sparse identification of nonlinear dynamical (SINDy) systems is adopted that is a regression algorithm to discover governing equations for nonlinear dynamical systems including fluid flows. In particular, SINDy uses sparse regression to determine the fewest terms in the governing equations required to accurately represent the data, and this results in parsimonious models that balance accuracy with model complexity to avoid overfitting.

MODEL RECTIFICATION. After model reduction, CFD model rectification may still be needed for each of the models in Phase 1 and 2 to capture unmodeled effects. This can be achieved by using a feed-forward term for cancelling unmodeled effects based on a regression model. This can be achieved using support vector regression over the error of the parsimonious CFD model relative to the experimental data.

REGRESSION. To enable rapid computation over the entire range of catheter tip and clot locations along the ICA and MCA, an interpolation map will be created for the expected sensed pressure for known excitation parameters based on the rectified parsimonious CFD model. There are several ways to achieve this, first, a thin-plate spline interpolation may be used, but to preserve the statistical covariance information, support vector regression (SVR) and GPR will be considered.

This regression process will also use information from image segmentation regarding the location of the catheter tip relative to the carotid syphon, which will be available from catheter tip tracking and manual segmentation of the cusp of the carotid syphon at the beginning of the procedure. Using parameters of excitation, specific geometric features of the vessel (e.g., diameters at select arc-lengths), and pressure readings the regressor will estimate the distance $L_c$.

Aneurysm wall contact A similar approach to the clot distance estimation will be followed, but in these experiments a soft semi-transparent small (3-7 mm) aneurysm model from United Biologics will be used and the size of the aneurysm will be varied. The data collection in the clot engagement case will be replicated, but the focus will be more on detecting catheter tip contact with the aneurysm wall. Aneurysm wall proximity will be determined using a 0.9 mm magnetic tracker marker that will be externally attached to the catheter and also used to digitize the depth at which contact with the aneurysm wall is verified visually.

Engagement quality. For these experiments, a straight blood vessel model will be used to minimize the effects of friction with the catheter. A standard aspiration catheter will be equipped with a clear tip made of clear plastic so it can be observed how the clot behaves after pulsed vacuum is applied when in contact with the catheter. Measurements of the catheter traction force when clot retrieval is attempted will be carried out using a high precision single axis load cell that will hold the mock vasculature carrying the clot. Two clot models will be used to compare the traction force of the catheter with a smooth vs. jagged surface. Clots for these experiment groups will be coagulated in the mock blood vessel with a filling rod having a smooth/jagged distal tip, respectively.

These two clot models will be used in the following two-group comparison of pulsatile versus constant vacuum. The first group of experiments will be carried out after applying a fixed vacuum of −27 inHg for three minutes following M. T. Frochler, "Comparison of Vacuum Pressures and Forces Generated by Different Catheters and Pumps for Aspiration Thrombectomy in Acute Ischemic Stroke," Interv. Neurol., vol. 6, no. 3-4, pp. 199-206, 2017, doi:

10.1159/000475478. The second group will be carried out for the same amount of engagement time, but using the pulsatile vacuum profile that terminates with a fixed vacuum of −27 inHg immediately preceding an attempt of clot retrieval. The catheter will then be withdrawn using a motorized stage while recording the vacuum levels and the traction force experienced by the mock blood vessel supporting the clot. During each experiment, vision data will be used to auto-annotate the data set with a flag indicating success or failure in clot retrieval. This data will be used for the testing of the success of the classification algorithm in predicting clot retrieval. Finally, data of both groups will be compared on the basis of maximal traction force measured and a t-test comparison will be carried out to discern statistically significant differences between the data sets.

The expected outcome of this characterization would be statistical models (distributions) that describe the variability in traction force across different conditions of clot surfaces for both smooth and jagged clot surfaces. Data from the pre- and post-engagement phases will be used to generate a classification outcome predicting whether the clot has been sufficiently engaged prior to a first attempt of clot retrieval.

The challenge in achieving this perception outcome is that, once a clot has engaged the catheter tip, the vacuum measurement alone is not a sufficient indicator for how well the clot has been dislodged and suctioned into the catheter tip. To overcome this challenge, we will first conduct many experiments where sensory data of vacuum, catheter tip motion, distance from clot, and maximal traction force achieved will be collated in a pre-operative statistical model. During a clot retrieval attempt, this model will be fused with the history of intra-operative sensory data to predict the anticipated quality engagement metric. Such information fusion can be achieved using product of distributions. Also, the pre-operative data will be used to train support vector (SV) classifier to predict whether a clot has been sufficiently engaged prior to an attempt of clot retrieval. SV classifiers will be used because they provide a method for classification for cases where the separation hyperplane between the classification groups is nonlinear. The robustness and favorable generalization properties with noisy data, coupled with a compact structure which allows real-time function estimation during motion control, motivate the choice of SV classifiers.

Using experimental data, labeled data sets will be created for training the SV classifiers. The data sets will be used for the jagged and smooth clot groups to investigate feature vector formations that improve classification outcome over the labeled training data sets. The classifiers will be evaluated on artificial data sets generated by including a pool of artificial data sets from the good and poor engagement experiments that were not included in the training phase. The accuracy of the algorithm in predicting good engagement and the correlation between the classifier prediction and the experimental success in clot retrieval will be tested.

Sensory feedback user interface. A graphical user interface (GUI) will be integrated into the proposed experimental setup to provide visual and auditory feedback to neurointerventionalists about catheter tip proximity to clots and the quality of clot engagement. The GUI will include a visualization of the frontal and lateral views of fluoroscopy imaging of the vasculature. These images will be obtained by transferring the output of the bi-plane fluoroscopy system to the GUI computer via a frame grabber (e.g., Sensoray 2255S). The GUI will enable the surgeon to manually digitize the clot location on the static image (roadmap), which is obtained by applying the "SmartMask" function to the digital subtraction angiography of the vasculature. Once the surgeon suspects proximity to a clot, they will initialize the pre-clot engagement sensing phase and the GUI will display sensed distance and emit a variable pitch sound as a function of proximity to clot interface. After the clot engagement, results of the classifier (good/poor engagement) will be displayed prior to clot retrieval attempt.

Figure 11:
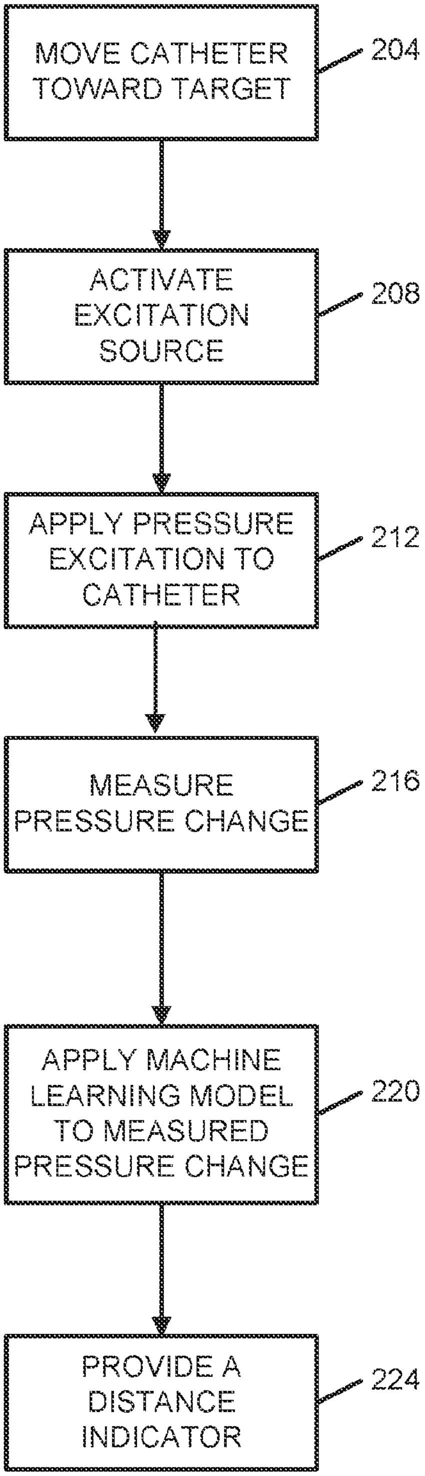
FIG. 11 illustrates a flowchart of a method for determining the distance between a tip of a catheter and a target.

FIG. 11 illustrates a flowchart of a method 200 for determining the distance between a tip of a catheter and a target. The method 200 is initiated when a patient presents with a condition, such as a stroke or an aneurysm, and is a candidate for a surgical procedure to retrieve a clot associated with such stroke or aneurysm. After the patient is prepped, a guidewire and catheter are inserted into the patient and moved (step 204) toward the target. The catheter is in fluid communication with a pressure sensor and an excitation source (e.g, a syringe) at the proximal end of the catheter. As the catheter approaches the target, the excitation source is activated (step 208) in a cyclical manner to apply flow and pressure excitation to the proximal end of the catheter (step 212). The pressure sensor measures a pressure change (step 216) at the proximal end of the catheter. The pressure change is based on a cycle of the applied proximal pressure excitation and advancement of the catheter toward the target. A processor (including, for example, a memory, non-transitory computer readable media to execute programs stored thereon to carry out various processes, peripheral components, a display, a communication interface, and the like) receives the pressure change measurements and applies a machine learning model to the measured pressure change (step 220) to determine the distance between the tip of the catheter and the target. The processor provides the distance between the tip of the catheter and the target to a user/surgeon (step 224). The processor may display a numerical value on the display representing the distance between the tip of the catheter and the target. Alternatively, the processor can initiate tactile feedback in the catheter and/or generate an audible signal representing how close the catheter tip is to the target and thereby representative of the distance between the catheter tip and the target as the tip moves toward the target. Further, the processor can provide a color bar (or other shape) that changes color (e.g., green, yellow, red) as the catheter tip approaches the target and is representative of the distance therebetween. In other alternatives, the processor can register and overlay an image (acquired via fluoroscopy during the procedure, for example) on a previously acquired vessel roadmap to show the distance between the tip of the catheter and the target. In some embodiments, the processor provides one or more of these distance indicators when the tip of the catheter is between 1 mm and 20 mm from the target. In other embodiments, the processor provides one or more of these distance indicators when the tip of the catheter is between 5 mm and 15 mm from the target.

Figure 12:
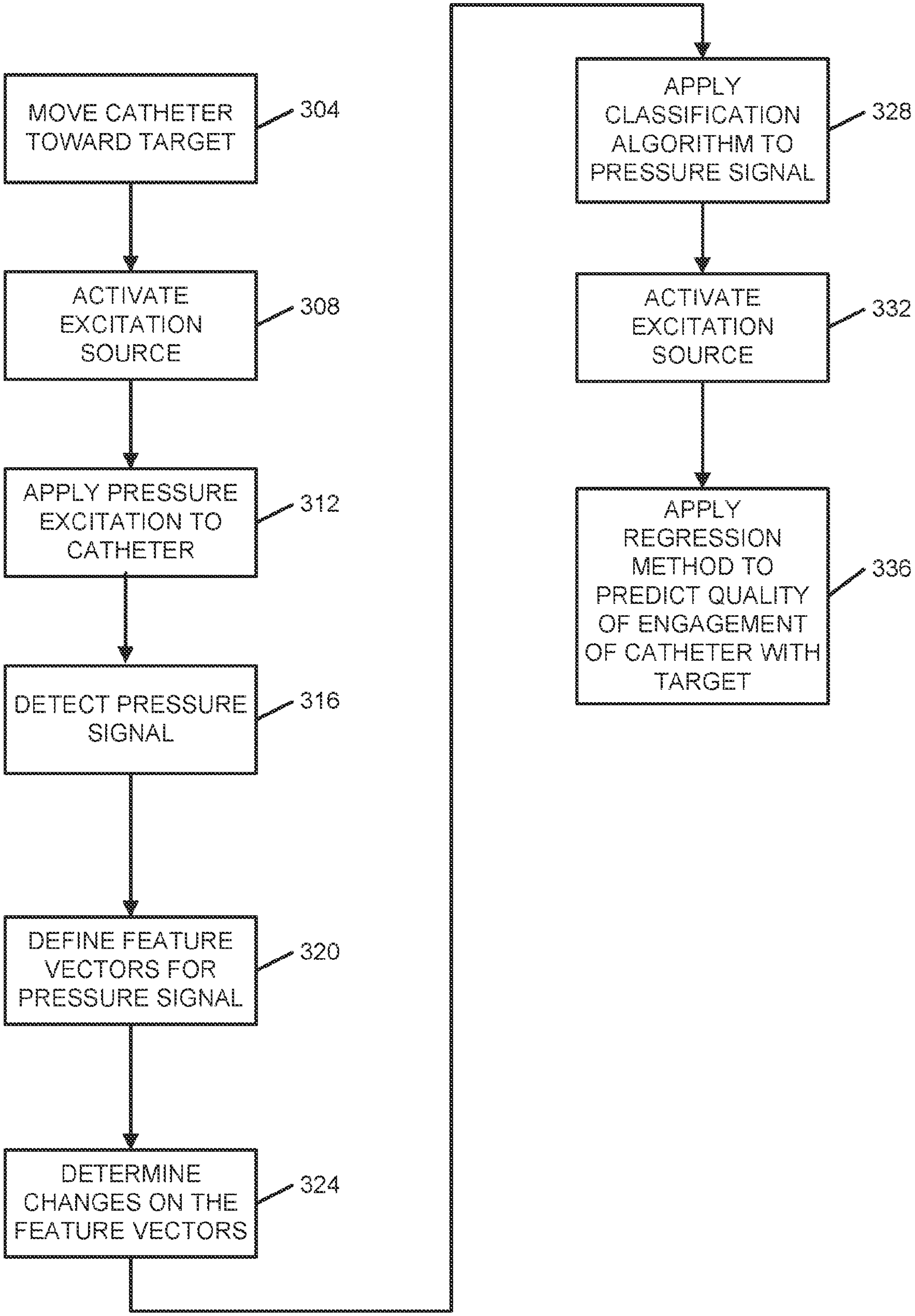
FIG. 12 illustrates a flowchart of a method of classifying quality of engagement between a tip of a catheter and a target.

FIG. 12 illustrates a flowchart of a method 300 of classifying quality of engagement between a tip of a catheter and a target. The method 300 is initiated when a patient presents with a condition, such as a stroke or an aneurysm, and is a candidate for a surgical procedure to retrieve a clot associated with such stroke or aneurysm. After the patient is prepped, a guidewire and catheter are inserted into the patient and moved (step 304) toward the target. The catheter is in fluid communication with a pressure sensor and an excitation source (e.g, a syringe) at the proximal end of the catheter. As the catheter approaches the target, the excitation source is activated (step 308) in a cyclical manner to apply flow and pressure excitation to the proximal end of the catheter (step 312). The pressure sensor detects a pressure signal (step 316) at the proximal end of the catheter. The pressure signal is based on a cycle of the applied proximal pressure excitation and advancement of the catheter toward the target. A processor (including, for example, a memory, non-transitory computer readable media to execute programs stored thereon to carry out various processes, peripheral components, a display, a communication interface, and the like) receives the pressure signal and defines feature vectors (e.g., pressure average within a cycle of excitation, pressure peaks, or area under the pressure signal as a function of piston motion) for the pressure signal (step 320) The processor also computes changes on one of the feature vectors within two cycles of incremental axial motion of the catheter (step 324) and then applies a classification algorithm to the pressure signal to determine whether the tip of the catheter is in contact with the target (step 328). If the processor determines that the tip of the catheter is in contact with the target, then the processor activates the excitation source (e.g., vacuum) to apply vacuum to promote catheter engagement with the target (step 332). The processor then applies a regression method (e.g., support vector regression, Gaussian process regression, or long-short term memory (LSTM) neural network) to predict quality (e.g., high, medium, or low) of engagement of the tip of the catheter with the target (step 336). Steps 216-224 may also occur within the method 300 to determine distance of the tip of the catheter from the target prior to catheter engagement with the target.

Various features of the invention are set forth in the following claims.

What is claimed is:

1. A method for determining a distance between a tip of a catheter and a target, the method comprising:
- advancing the catheter through vasculature toward the target in the vasculature;
- applying pulsatile flow and pressure excitation to a proximal end of the catheter as the catheter advances toward the target;
- measuring a pressure change, with a pressure sensor in fluid communication with the catheter, at the proximal end of the catheter, the pressure change based on a cycle of applied proximal pressure excitation and advancement of the catheter toward the target;
- providing the pressure change measurements to a processor, the pressure sensor in communication with the processor;
- applying, with the processor, a machine learning model to the measured pressure change to determine the distance between the tip of the catheter and the target, the machine learning model trained based on input data and a selection of features for classification including a reference pressure profile, a change in pressure profile relative to the reference pressure profile, and a flow resistance model as a function of viscosity, flow rate, catheter length, and diameter; and
- providing the distance between the tip of the catheter and the target to a user to inform the user whether to activate a vacuum at the proximal end of the catheter to engage the target.

2. The method of claim 1, wherein providing the distance between the tip of the catheter and the target includes providing an auditory signal to the user as the tip of the catheter approaches the target.

3. The method of claim 2, wherein the auditory signal is provided to the user when the tip of the catheter is between 1 mm and 20 mm from the target.

4. The method of claim 3, wherein the auditory signal is provided to the user when the tip of the catheter is between 5 mm and 15 mm from the target.

5. The method of claim 1, wherein providing the distance between the tip of the catheter and the target includes registering an image overlay on a vessel roadmap.

6. The method of claim 1, wherein providing the distance between the tip of the catheter and the target includes displaying a color bar with a numerical distance indicator, and wherein the color bar changes color with the change in distance as the tip of the catheter moves toward or away from the target.

7. The method of claim 1, further comprising determining if the tip of the catheter has engaged the target.

8. The method of claim 7, wherein determining if the tip of the catheter has engaged the target includes applying the machine learning model including support vector classification.

9. The method of claim 1, wherein the machine learning model is trained with a library of sample vessel geometries acquired by CT scans.

10. The method of claim 1, wherein the machine learning model is calibrated with vessel geometries corresponding with 95% confidence intervals of vessel diameters previously acquired.

11. The method of claim 1, further comprising applying a support vector regression curve to the machine learning model to generate a correlation between the pressure measurement and distance between the tip of the catheter and the target.

12. The method of claim 11, further comprising applying a machine learning classification model to confirm that the tip of the catheter is in contact with the target.

13. The method of claim 1, wherein the distance between the tip of the catheter and the target is 100 mm or less.

14. The method of claim 1, wherein the target includes a thrombus, an aneurysm wall, or a vascular wall within a vascular junction.

15. The method of claim 1, further comprising tuning parameters of the pressure excitation to evoke an axial motion at a distal end of the catheter for engagement of the tip of the catheter with the target.

16. The method of claim 1, further comprising providing a plurality of pressure measurements with the pressure sensor as the catheter advances toward the target.

17. A method of classifying quality of engagement between a tip of a catheter and a target, the method comprising:
- applying cyclic flow excitation to a proximal end of the catheter to displace a fraction of fluid contained within the catheter;
- measuring a pressure signal, with a pressure sensor in fluid communication with the catheter, at the proximal end of the catheter, the pressure change based on a cycle of applied excitation and advancement of the catheter toward the target, the pressure sensor in communication with an electronic processor;
- defining, with the electronic processor, feature vectors for the pressure signal;
- computing, with the electronic processor, changes in one of the feature vectors within two cycles of incremental axial motion of the catheter;
- applying, with the electronic processor, a classification algorithm to the pressure signal to determine whether the tip of the catheter is in contact with the target;

if the tip of the catheter is in contact with the target, applying vacuum excitation to promote catheter engagement with the target; and applying, with the electronic processor, a regression model to predict quality of engagement of the tip of the catheter with the target.

18. The method of claim 17, wherein the regression model includes support vector regression, Gaussian process regression, or long-short term memory (LSTM).

19. The method of claim 17, wherein the feature vectors include pressure average within a cycle of excitation, pressure peaks, or area under the pressure signal as a function of piston motion.

* * * * *